(12) United States Patent
Metzger et al.

(10) Patent No.: US 7,497,874 B1
(45) Date of Patent: Mar. 3, 2009

(54) KNEE JOINT PROSTHESIS

(75) Inventors: Robert Metzger, Wakarusa, IN (US);
Jacy C Hoeppner, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 582 days.

(21) Appl. No.: 10/934,282

(22) Filed: Sep. 3, 2004

Related U.S. Application Data

(63) Continuation-in-part of application No. 10/289,585, filed on Nov. 7, 2002, now Pat. No. 7,025,788, which is a continuation-in-part of application No. 09/792,172, filed on Feb. 23, 2001, now abandoned.

(51) Int. Cl.
*A61F 2/38* (2006.01)
(52) U.S. Cl. .................................... 623/20.15
(58) Field of Classification Search ................. 62/20.15, 62/20.36, 20.35, 20.25, 20.28, 20.27, 20.31, 62/22.45, 23.42
See application file for complete search history.

(56) References Cited

U.S. PATENT DOCUMENTS

| | | |
|---|---|---|
| 3,806,961 A | 4/1974 | Muller et al. |
| 3,848,272 A | 11/1974 | Noiles |
| 3,859,992 A | 1/1975 | Amstutz |
| 3,878,566 A | 4/1975 | Bechtol |
| 3,964,106 A | 6/1976 | Hutter, Jr. et al. |
| 4,001,897 A | 1/1977 | Rambert et al. |
| 4,007,495 A | 2/1977 | Frazier |
| 4,012,796 A | 3/1977 | Weisman et al. |
| 4,041,550 A | 8/1977 | Frazier |
| 4,151,615 A | 5/1979 | Hall |
| 4,202,055 A | 5/1980 | Reiner et al. |
| 4,224,698 A | 9/1980 | Hopson |
| 4,284,080 A | 8/1981 | Rehder et al. |
| 4,305,394 A | 12/1981 | Bertuch, Jr. |
| 4,344,192 A | 8/1982 | Imbert et al. |
| 4,404,691 A | 9/1983 | Buning et al. |
| 4,475,549 A | 10/1984 | Oh |
| RE31,865 E | 4/1985 | Roux et al. |
| 4,549,319 A | 10/1985 | Meyer |
| 4,579,558 A | 4/1986 | Ramer |

(Continued)

FOREIGN PATENT DOCUMENTS

DE    3336004    6/1985

(Continued)

OTHER PUBLICATIONS

International Search Report and Written Opinion for PCT/US2008/000374 mailed Jun. 6, 2008.

*Primary Examiner*—Brian E. Pellegrino
(74) *Attorney, Agent, or Firm*—Harness, Dickey & Pierce, P.L.C.

(57) ABSTRACT

A modular knee prosthesis includes a femoral stem having a proximal end portion. A femoral component includes a first engagement portion defined thereon wherein the femoral stem is selectively attachable to the first engagement portion of the femoral component. A connecting member includes a first end selectively attachable to the first engagement portion of the femoral component and includes a second engagement portion defined on a second end wherein the femoral stem is selectively attachable to the second engagement portion of the connecting member.

9 Claims, 15 Drawing Sheets

U.S. PATENT DOCUMENTS

| | | | |
|---|---|---|---|
| 4,619,658 A | 10/1986 | Pappas et al. | |
| 4,624,674 A | 11/1986 | Pappas et al. | |
| 4,632,111 A | 12/1986 | Roche | |
| 4,655,777 A | 4/1987 | Dunn et al. | |
| 4,661,112 A | 4/1987 | Muller et al. | |
| 4,676,797 A * | 6/1987 | Anapliotis et al. | 623/23.45 |
| 4,676,798 A | 6/1987 | Noiles | |
| 4,676,799 A | 6/1987 | Legrand et al. | |
| 4,698,063 A | 10/1987 | Link et al. | |
| 4,711,233 A | 12/1987 | Brown | |
| 4,714,477 A | 12/1987 | Fichera et al. | |
| 4,716,894 A | 1/1988 | Lazzeri et al. | |
| 4,718,911 A | 1/1988 | Kenna | |
| 4,718,915 A | 1/1988 | Epinette et al. | |
| 4,718,916 A | 1/1988 | Morscher et al. | |
| 4,728,333 A | 3/1988 | Masse et al. | |
| 4,737,411 A | 4/1988 | Graves, Jr. et al. | |
| 4,764,171 A | 8/1988 | Harder et al. | |
| 4,770,658 A | 9/1988 | Geremakis | |
| 4,770,659 A | 9/1988 | Kendall | |
| 4,770,660 A | 9/1988 | Averill | |
| 4,770,661 A | 9/1988 | Oh | |
| 4,778,474 A | 10/1988 | Homsy | |
| 4,784,662 A | 11/1988 | Muller et al. | |
| 4,784,663 A | 11/1988 | Kenna | |
| 4,790,852 A | 12/1988 | Noiles | |
| 4,790,854 A | 12/1988 | Harder et al. | |
| 4,795,470 A | 1/1989 | Goymann et al. | |
| 4,795,471 A | 1/1989 | Oh | |
| 4,798,610 A | 1/1989 | Averill et al. | |
| 4,801,301 A | 1/1989 | Noiles | |
| 4,813,961 A | 3/1989 | Sostegni et al. | |
| 4,822,366 A | 4/1989 | Bolesky | |
| 4,827,919 A | 5/1989 | Barbarito et al. | |
| 4,828,566 A | 5/1989 | Griss et al. | |
| 4,842,606 A | 6/1989 | Kranz et al. | |
| 4,846,840 A | 7/1989 | Leclercq et al. | |
| 4,851,007 A | 7/1989 | Gray | |
| 4,871,368 A | 10/1989 | Wagner et al. | |
| 4,878,916 A | 11/1989 | Rhenter et al. | |
| 4,883,492 A | 11/1989 | Frey et al. | |
| 4,888,021 A | 12/1989 | Forte et al. | |
| 4,904,265 A | 2/1990 | MacCollum et al. | |
| 4,908,033 A | 3/1990 | Frey et al. | |
| 4,908,034 A | 3/1990 | Weightman et al. | |
| 4,908,036 A | 3/1990 | Link et al. | |
| 4,911,723 A | 3/1990 | Menschik et al. | |
| 4,919,674 A | 4/1990 | Schelhas et al. | |
| 4,923,472 A | 5/1990 | Ugolini et al. | |
| 4,936,853 A | 6/1990 | Fabian et al. | |
| 4,936,855 A | 6/1990 | Sherman | |
| 4,936,861 A | 6/1990 | Muller et al. | |
| 4,938,769 A | 7/1990 | Shaw | |
| 4,938,772 A | 7/1990 | Frey et al. | |
| 4,944,756 A | 7/1990 | Kenna | |
| 4,944,757 A * | 7/1990 | Martinez et al. | 623/20.15 |
| 4,950,297 A | 8/1990 | Elloy et al. | |
| 4,950,298 A | 8/1990 | Gustilo et al. | |
| 4,950,299 A | 8/1990 | Noiles | |
| 4,960,427 A | 10/1990 | Noiles | |
| 4,961,748 A | 10/1990 | Frey et al. | |
| 4,963,154 A | 10/1990 | Anapliotis et al. | |
| 4,963,155 A | 10/1990 | Lazzeri et al. | |
| 4,964,869 A | 10/1990 | Auclair et al. | |
| 4,978,356 A | 12/1990 | Noiles | |
| 4,985,037 A | 1/1991 | Petersen | |
| 4,990,161 A | 2/1991 | Kampner | |
| 4,994,064 A | 2/1991 | Aboczky | |
| 4,995,883 A * | 2/1991 | Demane et al. | 623/22.42 |
| 5,002,578 A | 3/1991 | Luman | |
| 5,002,581 A | 3/1991 | Paxson et al. | |
| 5,009,666 A | 4/1991 | Van Syckle et al. | |
| 5,019,103 A | 5/1991 | Van Zile et al. | |
| 5,019,105 A | 5/1991 | Wiley | |
| 5,019,108 A | 5/1991 | Bertin et al. | |
| 5,021,062 A | 6/1991 | Adrey et al. | |
| 5,037,438 A | 8/1991 | Davidson | |
| 5,037,441 A | 8/1991 | Bouvet et al. | |
| 5,041,140 A | 8/1991 | Teinturier et al. | |
| 5,062,853 A | 11/1991 | Forte | |
| 5,074,879 A | 12/1991 | Pappas et al. | |
| 5,080,677 A | 1/1992 | Shelley et al. | |
| 5,084,051 A | 1/1992 | Tormala et al. | |
| 5,092,900 A | 3/1992 | Marchetti et al. | |
| 5,098,437 A | 3/1992 | Kashuba et al. | |
| 5,108,437 A | 4/1992 | Kenna | |
| 5,108,439 A | 4/1992 | Morscher et al. | |
| 5,108,445 A | 4/1992 | Ashby et al. | |
| 5,108,446 A | 4/1992 | Wagner et al. | |
| 5,108,450 A | 4/1992 | Horber et al. | |
| 5,116,378 A | 5/1992 | Carbone | |
| 5,116,379 A | 5/1992 | McLardy-Smith et al. | |
| 5,116,380 A | 5/1992 | Hewka et al. | |
| 5,133,760 A | 7/1992 | Petersen et al. | |
| 5,133,763 A | 7/1992 | Mullers et al. | |
| 5,137,535 A | 8/1992 | Keller | |
| 5,137,536 A | 8/1992 | Koshino et al. | |
| 5,147,406 A | 9/1992 | Houston et al. | |
| 5,152,796 A | 10/1992 | Slamin | |
| 5,152,797 A | 10/1992 | Luckman et al. | |
| 5,163,963 A | 11/1992 | Hewka et al. | |
| 5,169,399 A | 12/1992 | Ryland et al. | |
| 5,171,243 A | 12/1992 | Kashuba et al. | |
| 5,171,276 A | 12/1992 | Caspari et al. | |
| 5,171,286 A | 12/1992 | Lawes et al. | |
| 5,171,313 A | 12/1992 | Salyer | |
| 5,171,323 A | 12/1992 | Willert et al. | |
| 5,176,709 A | 1/1993 | Branemark et al. | |
| 5,180,394 A | 1/1993 | Davidson | |
| 5,181,925 A | 1/1993 | Houston et al. | |
| 5,181,929 A | 1/1993 | Prats et al. | |
| 5,192,331 A | 3/1993 | Spotorno et al. | |
| 5,194,066 A | 3/1993 | Van Zile | |
| 5,197,987 A | 3/1993 | Koch et al. | |
| 5,197,988 A | 3/1993 | Spotorno et al. | |
| 5,201,769 A | 4/1993 | Schutzer | |
| 5,211,664 A | 5/1993 | Tepic et al. | |
| 5,211,666 A | 5/1993 | Fetto | |
| 5,217,496 A | 6/1993 | Bruce et al. | |
| 5,217,498 A | 6/1993 | Henssge et al. | |
| 5,219,362 A | 6/1993 | Tuke et al. | |
| 5,222,983 A | 6/1993 | Schmitz et al. | |
| 5,222,984 A | 6/1993 | Forte | |
| 5,226,915 A | 7/1993 | Bertin | |
| 5,258,034 A | 11/1993 | Furlong et al. | |
| 5,258,035 A | 11/1993 | Hofmann et al. | |
| 5,263,988 A | 11/1993 | Huebner | |
| 5,275,601 A | 1/1994 | Gogolewski et al. | |
| 5,282,867 A | 2/1994 | Mikhail | |
| 5,282,870 A | 2/1994 | Moser et al. | |
| 5,290,311 A | 3/1994 | Baumann et al. | |
| 5,290,313 A | 3/1994 | Heldreth | |
| 5,290,315 A | 3/1994 | DeCarlo, Jr. | |
| 5,290,318 A | 3/1994 | Ling et al. | |
| 5,292,322 A | 3/1994 | Faccioli et al. | |
| 5,314,478 A | 5/1994 | Oka et al. | |
| 5,314,479 A | 5/1994 | Rockwood, Jr. et al. | |
| 5,314,491 A | 5/1994 | Thongpreda et al. | |
| 5,326,358 A | 7/1994 | Aubriot et al. | |
| 5,326,359 A | 7/1994 | Oudard et al. | |
| 5,330,534 A | 7/1994 | Herrington et al. | |
| 5,336,267 A | 8/1994 | Kubein-Meesenburg et al. | |
| 5,343,877 A | 9/1994 | Park | |
| 5,344,460 A | 9/1994 | Turanyi et al. | |

| Patent | Date | Inventor |
|---|---|---|
| 5,358,529 A | 10/1994 | Davidson |
| 5,360,449 A | 11/1994 | Branemark et al. |
| 5,360,451 A | 11/1994 | Keller et al. |
| 5,370,698 A | 12/1994 | Heimke et al. |
| 5,370,702 A | 12/1994 | Jones |
| 5,376,122 A | 12/1994 | Pappas et al. |
| 5,376,123 A | 12/1994 | Klaue et al. |
| 5,376,124 A | 12/1994 | Gustke et al. |
| 5,383,938 A | 1/1995 | Rohr et al. |
| 5,387,239 A | 2/1995 | Bianco et al. |
| 5,387,241 A | 2/1995 | Hayes |
| 5,405,392 A | 4/1995 | Deckner et al. |
| 5,405,400 A | 4/1995 | Linscheid et al. |
| 5,405,401 A | 4/1995 | Lippincott, III et al. |
| 5,405,403 A | 4/1995 | Mikhail |
| 5,413,610 A | 5/1995 | Amino et al. |
| 5,417,696 A | 5/1995 | Kashuba et al. |
| 5,425,779 A | 6/1995 | Schlosser et al. |
| 5,431,657 A | 7/1995 | Rohr |
| 5,443,512 A | 8/1995 | Parr et al. |
| 5,443,516 A | 8/1995 | Albrektsson et al. |
| 5,458,637 A | 10/1995 | Hayes |
| 5,462,563 A | 10/1995 | Shearer et al. |
| 5,480,443 A | 1/1996 | Elias |
| 5,480,444 A | 1/1996 | Incavo et al. |
| 5,480,445 A | 1/1996 | Burkinshaw |
| 5,480,446 A | 1/1996 | Goodfellow et al. |
| 5,480,447 A | 1/1996 | Skiba |
| 5,480,448 A | 1/1996 | Mikhail |
| 5,480,451 A | 1/1996 | Grundei et al. |
| 5,480,452 A | 1/1996 | Hofmann et al. |
| 5,486,181 A | 1/1996 | Cohen et al. |
| 5,489,311 A | 2/1996 | Cipolletti |
| 5,507,817 A | 4/1996 | Craig et al. |
| 5,507,818 A * | 4/1996 | McLaughlin ............ 623/23.42 |
| 5,507,820 A | 4/1996 | Pappas |
| 5,507,826 A | 4/1996 | Besselink et al. |
| 5,507,829 A | 4/1996 | Thongpreda et al. |
| 5,507,832 A | 4/1996 | Michielli et al. |
| 5,522,902 A | 6/1996 | Yuan et al. |
| 5,531,793 A | 7/1996 | Kelman et al. |
| 5,534,032 A | 7/1996 | Hodorek |
| 5,549,684 A | 8/1996 | Amino et al. |
| 5,549,685 A | 8/1996 | Hayes |
| 5,549,696 A | 8/1996 | Willi et al. |
| 5,549,699 A | 8/1996 | MacMahon et al. |
| 5,549,701 A | 8/1996 | Mikhail |
| 5,549,703 A | 8/1996 | Daigle et al. |
| 5,549,704 A | 8/1996 | Sutter et al. |
| 5,549,706 A | 8/1996 | McCarthy |
| 5,552,454 A | 9/1996 | Kretschmann et al. |
| 5,556,432 A | 9/1996 | Kubein-Meesenburg et al. |
| 5,556,433 A | 9/1996 | Gabriel et al. |
| 5,571,193 A | 11/1996 | Kampner |
| 5,571,194 A | 11/1996 | Gabriel |
| 5,571,196 A | 11/1996 | Stein |
| 5,571,201 A | 11/1996 | Averill et al. |
| 5,571,202 A | 11/1996 | Mathys, Sr. et al. |
| 5,580,352 A | 12/1996 | Sekel et al. |
| 5,584,837 A | 12/1996 | Petersen |
| 5,593,447 A | 1/1997 | Angeli et al. |
| 5,593,449 A | 1/1997 | Roberson, Jr. |
| 5,593,450 A | 1/1997 | Scott et al. |
| 5,593,451 A | 1/1997 | Averill et al. |
| 5,609,641 A | 3/1997 | Johnson et al. |
| 5,609,642 A * | 3/1997 | Johnson et al. ............ 606/88 |
| 5,609,645 A | 3/1997 | Vinciguerra |
| 5,609,647 A | 3/1997 | Kalberer et al. |
| 5,609,648 A | 3/1997 | Oehy et al. |
| 5,639,280 A | 6/1997 | Warner et al. |
| 5,641,323 A | 6/1997 | Caldarise |
| 5,645,593 A | 7/1997 | Woods et al. |
| 5,645,594 A | 7/1997 | Devanathan et al. |
| 5,645,604 A | 7/1997 | Schneider et al. |
| 5,653,765 A | 8/1997 | McTighe et al. |
| 5,658,344 A | 8/1997 | Hurlburt |
| 5,658,346 A | 8/1997 | Willi et al. |
| 5,658,348 A | 8/1997 | Rohr, Jr. |
| 5,658,349 A | 8/1997 | Brooks et al. |
| 5,676,700 A | 10/1997 | Black et al. |
| 5,676,704 A | 10/1997 | Ries et al. |
| 5,681,354 A | 10/1997 | Eckhoff |
| 5,683,399 A | 11/1997 | Jones |
| 5,683,472 A | 11/1997 | O'Neil et al. |
| 5,702,463 A | 12/1997 | Pothier et al. |
| 5,702,482 A | 12/1997 | Thongpreda et al. |
| 5,702,487 A | 12/1997 | Averill et al. |
| 5,725,589 A | 3/1998 | Pfaff et al. |
| 5,725,591 A | 3/1998 | DeCarlo, Jr. et al. |
| 5,725,597 A | 3/1998 | Hwang et al. |
| 5,735,901 A | 4/1998 | Maumy et al. |
| 5,746,771 A | 5/1998 | Clement, Jr. et al. |
| 5,749,877 A | 5/1998 | Young et al. |
| 5,755,805 A | 5/1998 | Whiteside |
| 5,755,807 A | 5/1998 | Anstaett et al. |
| 5,755,808 A | 5/1998 | DeCarlo et al. |
| 5,766,255 A | 6/1998 | Slamin et al. |
| 5,766,256 A | 6/1998 | Oudard et al. |
| 5,766,260 A | 6/1998 | Whiteside |
| 5,766,262 A | 6/1998 | Mikhail |
| 5,776,200 A | 7/1998 | Johnson et al. |
| 5,776,201 A | 7/1998 | Colleran et al. |
| 5,776,202 A | 7/1998 | Copf et al. |
| 5,782,920 A * | 7/1998 | Colleran .................. 623/20.34 |
| 5,782,921 A | 7/1998 | Colleran et al. |
| 5,782,924 A | 7/1998 | Johnson |
| 5,782,930 A | 7/1998 | Lin et al. |
| 5,800,554 A | 9/1998 | Scholz et al. |
| 5,800,555 A | 9/1998 | Gray, III |
| 5,800,556 A | 9/1998 | Sanders et al. |
| 5,800,558 A | 9/1998 | LaHaise, Sr. |
| 5,800,560 A | 9/1998 | Draenert et al. |
| 5,817,096 A | 10/1998 | Salyer |
| 5,824,097 A * | 10/1998 | Gabriel et al. ............ 623/23.15 |
| 5,824,107 A | 10/1998 | Tschirren et al. |
| 5,824,108 A | 10/1998 | Huebner |
| 5,858,020 A | 1/1999 | Johnson et al. |
| 5,865,850 A | 2/1999 | Matthews |
| 5,871,547 A | 2/1999 | Abouaf et al. |
| 5,879,387 A | 3/1999 | Jones et al. |
| 5,879,390 A | 3/1999 | Kubein-Meesenburg et al. |
| 5,879,391 A | 3/1999 | Slamin |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,406 A | 3/1999 | Lilley |
| 5,888,205 A | 3/1999 | Pratt et al. |
| 5,888,206 A | 3/1999 | Lob et al. |
| 5,888,211 A | 3/1999 | Sanders |
| 5,899,942 A | 5/1999 | Berman |
| 5,902,340 A | 5/1999 | White et al. |
| 5,904,688 A | 5/1999 | Gilbert et al. |
| 5,904,720 A | 5/1999 | Farrar et al. |
| 5,906,644 A | 5/1999 | Powell |
| 5,916,269 A | 6/1999 | Serbousek et al. |
| 5,916,270 A | 6/1999 | Lipman |
| 5,919,236 A | 7/1999 | Pfaff et al. |
| 5,928,286 A | 7/1999 | Ashby et al. |
| 5,935,171 A | 8/1999 | Schneider et al. |
| 5,935,175 A | 8/1999 | Ostiguy, Jr. et al. |
| 5,938,702 A | 8/1999 | Lopez et al. |
| 5,944,756 A | 8/1999 | Fischetti et al. |
| 5,944,759 A | 8/1999 | Link et al. |
| 5,951,603 A | 9/1999 | O'Neil et al. |

| Patent No. | Kind | Date | Inventor(s) |
|---|---|---|---|
| 5,954,727 | A | 9/1999 | Collazo |
| 5,957,979 | A | 9/1999 | Beckman et al. |
| 5,961,516 | A | 10/1999 | Graf et al. |
| 5,973,222 | A | 10/1999 | Devanathan et al. |
| 5,976,148 | A | 11/1999 | Charpenet et al. |
| 5,976,188 | A | 11/1999 | Dextradeur et al. |
| 5,976,189 | A | 11/1999 | Keller et al. |
| 5,977,204 | A | 11/1999 | Boyan et al. |
| 5,980,574 | A | 11/1999 | Takei et al. |
| 5,984,968 | A | 11/1999 | Park |
| 5,984,969 | A | 11/1999 | Matthews et al. |
| 5,989,293 | A | 11/1999 | Cook et al. |
| 5,989,294 | A | 11/1999 | Marlow et al. |
| 5,997,576 | A | 12/1999 | Copf et al. |
| 5,997,577 | A | 12/1999 | Herrington et al. |
| 5,997,579 | A | 12/1999 | Albrektsson et al. |
| 6,004,353 | A | 12/1999 | Masini |
| 6,005,018 | A | 12/1999 | Cicierega et al. |
| 6,007,580 | A | 12/1999 | Lehto et al. |
| 6,008,432 | A | 12/1999 | Taylor |
| 6,010,533 | A | 1/2000 | Pope et al. |
| 6,010,534 | A | 1/2000 | O'Neil et al. |
| 6,013,103 | A | 1/2000 | Kaufman et al. |
| 6,013,104 | A | 1/2000 | Kampner |
| 6,015,937 | A | 1/2000 | Branemark et al. |
| 6,027,505 | A | 2/2000 | Peter et al. |
| 6,039,764 | A | 3/2000 | Pottenger et al. |
| 6,042,611 | A | 3/2000 | Noiles |
| 6,045,583 | A | 4/2000 | Gross et al. |
| 6,053,945 | A | 4/2000 | O'Neil et al. |
| 6,056,779 | A | 5/2000 | Noyer et al. |
| 6,059,833 | A | 5/2000 | Doets et al. |
| 6,063,091 | A | 5/2000 | Lombardo et al. |
| 6,063,124 | A | 5/2000 | Amstutz |
| 6,066,176 | A | 5/2000 | Oshida |
| 6,071,311 | A | 6/2000 | O'Neil et al. |
| 6,074,424 | A | 6/2000 | Perrone, Jr. et al. |
| 6,074,425 | A | 6/2000 | Pappas |
| 6,086,614 | A | 7/2000 | Mumme |
| 6,087,553 | A | 7/2000 | Cohen et al. |
| 6,090,146 | A * | 7/2000 | Rozow et al. ............ 623/22.42 |
| 6,093,208 | A | 7/2000 | Tian et al. |
| 6,096,082 | A | 8/2000 | Stegmuller et al. |
| 6,099,569 | A | 8/2000 | Keller et al. |
| 6,099,571 | A | 8/2000 | Knapp |
| 6,113,640 | A | 9/2000 | Tormala et al. |
| 6,117,175 | A | 9/2000 | Bosredon et al. |
| 6,120,543 | A | 9/2000 | Kubein-Meesenburg et al. |
| 6,120,545 | A | 9/2000 | Hamelijnck et al. |
| 6,126,690 | A | 10/2000 | Ateshian et al. |
| 6,126,691 | A | 10/2000 | Kasra et al. |
| 6,126,692 | A | 10/2000 | Robie et al. |
| 6,126,693 | A | 10/2000 | O'Neil et al. |
| 6,126,694 | A | 10/2000 | Gray, Jr. |
| 6,126,695 | A | 10/2000 | Semlitsch et al. |
| 6,129,765 | A | 10/2000 | Lopez et al. |
| 6,132,468 | A | 10/2000 | Mansmann |
| 6,132,469 | A | 10/2000 | Schroeder |
| 6,136,033 | A | 10/2000 | Suemer et al. |
| 6,136,035 | A | 10/2000 | Lob et al. |
| 6,139,584 | A | 10/2000 | Ochoa et al. |
| 6,146,424 | A | 11/2000 | Gray, Jr. et al. |
| 6,149,687 | A | 11/2000 | Gray, Jr. et al. |
| 6,152,930 | A | 11/2000 | Mastrorio |
| 6,152,961 | A | 11/2000 | Ostiguy, Jr. et al. |
| 6,156,070 | A | 12/2000 | Incavo et al. |
| 6,162,255 | A | 12/2000 | Oyola |
| 6,162,256 | A | 12/2000 | Ostiguy, Jr. et al. |
| 6,165,220 | A | 12/2000 | McKellop et al. |
| 6,165,222 | A | 12/2000 | Hoeppner et al. |
| 6,168,600 | B1 | 1/2001 | Grace et al. |
| 6,171,342 | B1 | 1/2001 | O'Neil |
| 6,179,876 | B1 | 1/2001 | Stamper et al. |
| 6,179,877 | B1 | 1/2001 | Burke |
| 6,193,759 | B1 | 2/2001 | Ro et al. |
| 6,197,032 | B1 | 3/2001 | Lawes et al. |
| 6,200,324 | B1 | 3/2001 | Regni, Jr. |
| 6,206,929 | B1 | 3/2001 | Ochoa et al. |
| 6,214,014 | B1 | 4/2001 | McGann |
| 6,214,052 | B1 | 4/2001 | Burkinshaw |
| 6,214,053 | B1 | 4/2001 | Ling et al. |
| 6,217,615 | B1 | 4/2001 | Sioshansi et al. |
| 6,217,619 | B1 | 4/2001 | Keller |
| 6,221,110 | B1 | 4/2001 | Copf et al. |
| 6,224,633 | B1 | 5/2001 | Kalberer et al. |
| 6,228,091 | B1 | 5/2001 | Lombardo et al. |
| 6,228,121 | B1 | 5/2001 | Khalili |
| 6,231,611 | B1 | 5/2001 | Mosseri et al. |
| 6,235,060 | B1 | 5/2001 | Kubein-Meesenburg et al. |
| 6,245,111 | B1 | 6/2001 | Shaffner |
| 6,248,132 | B1 | 6/2001 | Harris |
| 6,264,698 | B1 | 7/2001 | Lawes et al. |
| 6,264,699 | B1 | 7/2001 | Noiles et al. |
| 6,267,785 | B1 | 7/2001 | Masini |
| 6,281,264 | B1 | 8/2001 | Salovey et al. |
| 6,284,001 | B1 | 9/2001 | Knapp |
| 6,290,726 | B1 | 9/2001 | Pope et al. |
| 6,290,727 | B1 | 9/2001 | Otto et al. |
| 6,293,971 | B1 | 9/2001 | Nelson et al. |
| 6,296,667 | B1 | 10/2001 | Johnson et al. |
| 6,302,890 | B1 | 10/2001 | Leone, Jr. |
| 6,306,172 | B1 | 10/2001 | O'Neil |
| 6,319,285 | B1 | 11/2001 | Chamier et al. |
| 6,325,829 | B1 | 12/2001 | Schmotzer et al. |
| 6,334,875 | B1 | 1/2002 | Keller et al. |
| 6,340,370 | B1 | 1/2002 | Willert et al. |
| 6,342,075 | B1 | 1/2002 | MacArthur |
| 6,344,060 | B1 | 2/2002 | Schmotzer et al. |
| 6,344,496 | B1 | 2/2002 | Niederauer et al. |
| 6,352,559 | B1 | 3/2002 | Church et al. |
| 6,358,282 | B1 | 3/2002 | Wymann et al. |
| 6,361,566 | B1 | 3/2002 | Al-Hafez et al. |
| 6,368,354 | B2 | 4/2002 | Burstein et al. |
| 6,376,573 | B1 | 4/2002 | White et al. |
| 6,379,389 | B1 | 4/2002 | Koch et al. |
| 6,383,227 | B1 | 5/2002 | Baroud et al. |
| 6,387,131 | B1 | 5/2002 | Miehlke et al. |
| 6,413,280 | B1 | 7/2002 | Feiler |
| 6,416,552 | B1 | 7/2002 | Hoeppner et al. |
| 6,423,096 | B1 | 7/2002 | Musset et al. |
| 6,425,921 | B1 | 7/2002 | Grundei et al. |
| 6,428,578 | B2 * | 8/2002 | White ..................... 623/23.22 |
| 6,432,141 | B1 | 8/2002 | Stocks et al. |
| 6,436,145 | B1 | 8/2002 | Miller |
| 6,436,146 | B1 | 8/2002 | Hassler et al. |
| 6,447,549 | B1 | 9/2002 | Taft |
| 6,447,550 | B1 | 9/2002 | Hunter et al. |
| 6,451,058 | B2 | 9/2002 | Tuke et al. |
| 6,468,281 | B1 | 10/2002 | Badorf et al. |
| 6,475,243 | B1 | 11/2002 | Sheldon et al. |
| 6,482,237 | B2 | 11/2002 | Mosseri et al. |
| 6,488,713 | B1 | 12/2002 | Hershberger |
| 6,488,715 | B1 | 12/2002 | Pope et al. |
| 6,491,726 | B2 | 12/2002 | Pappas |
| 6,494,914 | B2 | 12/2002 | Brown et al. |
| 6,497,728 | B2 | 12/2002 | Yong et al. |
| 6,500,208 | B1 | 12/2002 | Metzger et al. |
| 6,503,281 | B1 | 1/2003 | Mallory |
| 6,506,215 | B1 | 1/2003 | Letot et al. |
| 6,517,583 | B1 | 2/2003 | Pope et al. |
| 6,518,328 | B2 | 2/2003 | Kumar |
| 6,520,995 | B2 | 2/2003 | Church et al. |
| 6,524,344 | B2 | 2/2003 | Yoon et al. |
| 6,524,345 | B2 | 2/2003 | Valimaa et al. |
| 6,527,807 | B1 * | 3/2003 | O'Neil et al. ............ 623/20.15 |
| 6,527,808 | B1 | 3/2003 | Albertorio et al. |

| | | | | | |
|---|---|---|---|---|---|
| 6,527,809 B1 | 3/2003 | Doursounian et al. | 6,953,479 B2 * | 10/2005 | Carson et al. ............ 623/20.15 |
| 6,527,810 B2 | 3/2003 | Johnson et al. | 6,962,607 B2 | 11/2005 | Gundlapalli et al. |
| 6,537,321 B1 | 3/2003 | Horber et al. | 6,966,932 B1 | 11/2005 | Schroeder |
| 6,540,786 B2 | 4/2003 | Chibrac et al. | 6,969,406 B2 | 11/2005 | Tornier et al. |
| 6,558,427 B2 | 5/2003 | Leclercq et al. | 6,972,021 B2 | 12/2005 | Raugel et al. |
| 6,565,575 B2 | 5/2003 | Lewis | 6,981,991 B2 | 1/2006 | Ferree |
| 6,565,606 B1 | 5/2003 | Bruce et al. | 7,004,946 B2 | 2/2006 | Parker et al. |
| 6,589,248 B1 | 7/2003 | Hughes | 7,022,142 B2 | 4/2006 | Johnson |
| 6,589,283 B1 | 7/2003 | Metzger et al. | 7,025,788 B2 | 4/2006 | Metzger et al. |
| 6,589,284 B1 | 7/2003 | Silberer et al. | 7,037,310 B2 | 5/2006 | Murphy |
| 6,602,259 B1 | 8/2003 | Masini | 7,044,974 B2 | 5/2006 | Garber et al. |
| 6,610,097 B2 | 8/2003 | Serbousek et al. | 7,051,417 B2 | 5/2006 | Michelson |
| 6,613,092 B1 | 9/2003 | Kana et al. | 7,056,577 B1 | 6/2006 | Bruce et al. |
| 6,616,696 B1 | 9/2003 | Merchant | 7,070,622 B1 | 7/2006 | Brown et al. |
| 6,620,198 B2 | 9/2003 | Burstein et al. | 7,074,241 B2 | 7/2006 | McKinnon |
| 6,623,488 B1 | 9/2003 | Leone, Jr. | 7,105,026 B2 | 9/2006 | Johnson et al. |
| 6,626,950 B2 | 9/2003 | Brown et al. | 7,108,719 B2 | 9/2006 | Horber et al. |
| 6,629,999 B1 | 10/2003 | Serafin, Jr. | 7,131,995 B2 | 11/2006 | Biedermann et al. |
| 6,641,617 B1 | 11/2003 | Merrill et al. | 7,153,326 B1 | 12/2006 | Metzger |
| 6,652,533 B2 | 11/2003 | O'Neil | 7,156,880 B2 | 1/2007 | Evans et al. |
| 6,652,586 B2 | 11/2003 | Hunter et al. | 7,166,133 B2 | 1/2007 | Evans et al. |
| 6,652,589 B2 | 11/2003 | Schmotzer et al. | 7,189,263 B2 | 3/2007 | Erbe et al. |
| 6,652,590 B1 | 11/2003 | Zitnansky et al. | 7,192,448 B2 | 3/2007 | Ferree |
| 6,660,040 B2 | 12/2003 | Chan et al. | 7,198,642 B2 * | 4/2007 | Hazebrouck et al. ..... 623/16.11 |
| 6,679,890 B2 | 1/2004 | Margulies et al. | 2001/0014828 A1 | 8/2001 | Yoon |
| 6,682,566 B2 | 1/2004 | Draenert et al. | 2001/0014829 A1 | 8/2001 | Yoon |
| 6,682,567 B1 | 1/2004 | Schroeder | 2001/0016780 A1 | 8/2001 | Yong San |
| 6,692,531 B1 | 2/2004 | Yoon et al. | 2001/0018616 A1 | 8/2001 | Schwab |
| 6,699,293 B2 * | 3/2004 | White ................... 623/23.22 | 2001/0039456 A1 | 11/2001 | Boyer et al. |
| 6,706,071 B1 | 3/2004 | Wolter et al. | 2001/0039457 A1 | 11/2001 | Boyer et al. |
| 6,706,072 B2 | 3/2004 | Dwyer et al. | 2001/0041941 A1 | 11/2001 | Boyer et al. |
| 6,712,857 B1 | 3/2004 | Roger et al. | 2001/0051830 A1 | 12/2001 | Tuke et al. |
| 6,712,858 B1 | 3/2004 | Grundei et al. | 2002/0022889 A1 | 2/2002 | Chibrac et al. |
| 6,716,248 B2 | 4/2004 | Huene | 2002/0022890 A1 | 2/2002 | Jacobsson et al. |
| 6,719,800 B2 | 4/2004 | Meyers et al. | 2002/0040244 A1 | 4/2002 | Despres et al. |
| 6,723,129 B2 | 4/2004 | Dwyer et al. | 2002/0040245 A1 | 4/2002 | Lester et al. |
| 6,726,725 B2 | 4/2004 | Hunter et al. | 2002/0042656 A1 | 4/2002 | Hunter et al. |
| 6,743,258 B1 | 6/2004 | Keller et al. | 2002/0045949 A1 | 4/2002 | Ling et al. |
| 6,755,864 B1 | 6/2004 | Brack et al. | 2002/0052659 A1 | 5/2002 | Hayes et al. |
| 6,758,864 B2 | 7/2004 | Storer et al. | 2002/0059000 A1 | 5/2002 | Dwyer et al. |
| 6,761,741 B2 | 7/2004 | Iesaka | 2002/0068980 A1 | 6/2002 | Serbousek et al. |
| 6,764,516 B2 | 7/2004 | Pappas | 2002/0072799 A1 | 6/2002 | Despres et al. |
| 6,770,097 B2 | 8/2004 | Leclercq et al. | 2002/0107577 A1 | 8/2002 | Storer et al. |
| 6,783,550 B2 | 8/2004 | MacArthur | 2002/0116068 A1 | 8/2002 | McLean |
| 6,786,933 B2 | 9/2004 | Merrill et al. | 2002/0120340 A1 * | 8/2002 | Metzger et al. .......... 623/20.15 |
| 6,793,681 B1 | 9/2004 | Pope et al. | 2002/0120341 A1 | 8/2002 | Stumpo et al. |
| 6,800,670 B2 | 10/2004 | Shen et al. | 2002/0138148 A1 | 9/2002 | Hyde |
| 6,802,866 B2 | 10/2004 | Bunz et al. | 2002/0138151 A1 | 9/2002 | Hubbard et al. |
| 6,811,568 B2 | 11/2004 | Minamikawa et al. | 2002/0143402 A1 | 10/2002 | Steinberg |
| 6,811,569 B1 | 11/2004 | Afriat et al. | 2002/0143403 A1 | 10/2002 | Vaidyanathan et al. |
| 6,818,019 B2 | 11/2004 | Horber et al. | 2002/0151978 A1 | 10/2002 | Zacouto et al. |
| 6,818,020 B2 | 11/2004 | Sun et al. | 2002/0156536 A1 | 10/2002 | Harris et al. |
| 6,827,739 B2 | 12/2004 | Griner et al. | 2002/0165615 A1 | 11/2002 | Abouaf et al. |
| 6,827,742 B2 | 12/2004 | Hayes, Jr. et al. | 2002/0173853 A1 | 11/2002 | Corl et al. |
| 6,840,944 B2 | 1/2005 | Suddaby | 2003/0009234 A1 | 1/2003 | Treacy et al. |
| 6,843,805 B2 | 1/2005 | Webb et al. | 2003/0014120 A1 | 1/2003 | Carson et al. |
| 6,843,806 B2 | 1/2005 | Hayes, Jr. et al. | 2003/0033018 A1 | 2/2003 | Merchant |
| 6,863,692 B2 | 3/2005 | Meulink | 2003/0040805 A1 | 2/2003 | Minamikawa |
| 6,866,683 B2 * | 3/2005 | Gerbec et al. ............ 623/18.11 | 2003/0050703 A1 | 3/2003 | Harris et al. |
| 6,866,685 B2 | 3/2005 | Chan et al. | 2003/0050705 A1 | 3/2003 | Cueille et al. |
| 6,869,447 B2 | 3/2005 | Lee et al. | 2003/0055508 A1 | 3/2003 | Metzger et al. |
| 6,875,237 B2 | 4/2005 | Dye | 2003/0055509 A1 | 3/2003 | McCue et al. |
| 6,881,229 B2 | 4/2005 | Khandkar et al. | 2003/0060890 A1 | 3/2003 | Tarabishy |
| 6,887,276 B2 | 5/2005 | Gerbec et al. | 2003/0065397 A1 | 4/2003 | Hanssen et al. |
| 6,905,515 B1 | 6/2005 | Gilbertson | 2003/0074078 A1 | 4/2003 | Doubler et al. |
| 6,908,486 B2 | 6/2005 | Lewallen | 2003/0093156 A1 | 5/2003 | Metzger et al. |
| 6,916,340 B2 | 7/2005 | Metzger et al. | 2003/0105529 A1 | 6/2003 | Synder et al. |
| 6,916,341 B2 | 7/2005 | Rolston | 2003/0109933 A1 | 6/2003 | Weissman et al. |
| 6,923,833 B2 | 8/2005 | Wasielewski | 2003/0114934 A1 | 6/2003 | Steinberg |
| 6,926,738 B2 | 8/2005 | Wyss | 2003/0114935 A1 | 6/2003 | Chan et al. |
| 6,926,739 B1 | 8/2005 | O'Connor et al. | 2003/0120346 A1 | 6/2003 | Mercinek et al. |
| 6,926,740 B2 | 8/2005 | Lewis et al. | 2003/0120347 A1 | 6/2003 | Steinberg |
| 6,944,518 B2 | 9/2005 | Roose | 2003/0125810 A1 | 7/2003 | Sullivan et al. |

| | | | | | | |
|---|---|---|---|---|---|---|
| 2003/0130740 A1 | 7/2003 | Stocks et al. | | 2005/0010303 A1 | 1/2005 | Nogier |
| 2003/0139818 A1 | 7/2003 | Rogers et al. | | 2005/0010304 A1 | 1/2005 | Jamali |
| 2003/0149485 A1 | 8/2003 | Tornier | | 2005/0021149 A1 | 1/2005 | Borruto et al. |
| 2003/0153981 A1 | 8/2003 | Wang et al. | | 2005/0027302 A1 | 2/2005 | Cueille et al. |
| 2003/0153982 A1 | 8/2003 | Pria | | 2005/0033442 A1 | 2/2005 | Fisher et al. |
| 2003/0158606 A1 | 8/2003 | Coon et al. | | 2005/0033445 A1 | 2/2005 | Siebel |
| 2003/0163202 A1 | 8/2003 | Lakin | | 2005/0038443 A1 | 2/2005 | Hedley et al. |
| 2003/0171815 A1 | 9/2003 | Kana et al. | | 2005/0043807 A1 | 2/2005 | Wood |
| 2003/0171817 A1 | 9/2003 | Rambert et al. | | 2005/0043812 A1 | 2/2005 | Corl et al. |
| 2003/0181984 A1 | 9/2003 | Abendschein | | 2005/0049524 A1 | 3/2005 | Lefevre et al. |
| 2003/0181987 A1 | 9/2003 | Muirhead-Allwood | | 2005/0049713 A1 | 3/2005 | Garber et al. |
| 2003/0204262 A1 | 10/2003 | Ferguson et al. | | 2005/0055102 A1 | 3/2005 | Tornier et al. |
| 2003/0204263 A1 | 10/2003 | Justin et al. | | 2005/0059972 A1 | 3/2005 | Biscup |
| 2003/0204268 A1 | 10/2003 | Gerbec et al. | | 2005/0060040 A1 | 3/2005 | Auxepaules et al. |
| 2003/0204269 A1 | 10/2003 | Gerbec et al. | | 2005/0071014 A1 | 3/2005 | Barnett et al. |
| 2003/0208276 A1 | 11/2003 | Berelsman et al. | | 2005/0071015 A1 | 3/2005 | Sekel |
| 2003/0220697 A1 | 11/2003 | Justin et al. | | 2005/0075641 A1 | 4/2005 | Yoon |
| 2003/0225457 A1 | 12/2003 | Justin et al. | | 2005/0080490 A1 | 4/2005 | Bertram |
| 2003/0225458 A1 | 12/2003 | Donkers et al. | | 2005/0085823 A1 | 4/2005 | Murphy |
| 2003/0229398 A1 | 12/2003 | Iesaka | | 2005/0090903 A1 | 4/2005 | Khandkar et al. |
| 2004/0002766 A1 | 1/2004 | Hunter et al. | | 2005/0102032 A1 | 5/2005 | Beynnon et al. |
| 2004/0019380 A1 | 1/2004 | Baege et al. | | 2005/0102033 A1 | 5/2005 | Lambert et al. |
| 2004/0019382 A1 | 1/2004 | Amirouche et al. | | 2005/0102034 A1 | 5/2005 | Hayes et al. |
| 2004/0019386 A1 | 1/2004 | Ferree | | 2005/0102038 A1 | 5/2005 | Grundei |
| 2004/0024460 A1 | 2/2004 | Ferree | | 2005/0107884 A1 | 5/2005 | Johnson et al. |
| 2004/0030394 A1 | 2/2004 | Horber | | 2005/0119755 A1 | 6/2005 | Kristensen |
| 2004/0030400 A1 | 2/2004 | Horber | | 2005/0125067 A1 | 6/2005 | Sweeney |
| 2004/0039449 A1 | 2/2004 | Tornier | | 2005/0131540 A1 | 6/2005 | Trieu |
| 2004/0039451 A1 | 2/2004 | Southworth | | 2005/0137603 A1 | 6/2005 | Belew et al. |
| 2004/0049284 A1 | 3/2004 | German et al. | | 2005/0137708 A1 | 6/2005 | Clark |
| 2004/0049285 A1 | 3/2004 | Haas | | 2005/0137711 A1 | 6/2005 | Southworth et al. |
| 2004/0049286 A1 | 3/2004 | German et al. | | 2005/0143828 A1 | 6/2005 | Collins et al. |
| 2004/0054418 A1 | 3/2004 | McLean et al. | | 2005/0143835 A1 | 6/2005 | Gilbertson |
| 2004/0059427 A1 | 3/2004 | Serbousek et al. | | 2005/0143836 A1 | 6/2005 | Steinberg |
| 2004/0068324 A1 | 4/2004 | Grundei | | 2005/0149043 A1 | 7/2005 | Parry et al. |
| 2004/0073315 A1 | 4/2004 | Justin et al. | | 2005/0149047 A1 | 7/2005 | Parry et al. |
| 2004/0078083 A1 | 4/2004 | Gibbs et al. | | 2005/0154470 A1 | 7/2005 | Sekel |
| 2004/0083004 A1 | 4/2004 | Wasielewski | | 2005/0154471 A1 | 7/2005 | Aram et al. |
| 2004/0098133 A1 | 5/2004 | Carignan et al. | | 2005/0165490 A1 | 7/2005 | Tornier |
| 2004/0098134 A1 | 5/2004 | Meulink | | 2005/0165491 A1 | 7/2005 | Diaz |
| 2004/0102851 A1 | 5/2004 | Saladino | | 2005/0165492 A1 | 7/2005 | Fitz |
| 2004/0102852 A1 | 5/2004 | Johnson et al. | | 2005/0171612 A1 | 8/2005 | Rolston |
| 2004/0107594 A1 | 6/2004 | Afriat | | 2005/0177172 A1 | 8/2005 | Acker et al. |
| 2004/0117023 A1 | 6/2004 | Gerbec et al. | | 2005/0177242 A1 | 8/2005 | Lotke |
| 2004/0117029 A1 | 6/2004 | Lewis et al. | | 2005/0177244 A1 | 8/2005 | Steinberg |
| 2004/0122521 A1 | 6/2004 | Lee et al. | | 2005/0187635 A1 | 8/2005 | Metzger |
| 2004/0143336 A1 | 7/2004 | Burkinshaw | | 2005/0187637 A1 | 8/2005 | Karrer et al. |
| 2004/0143341 A1 | 7/2004 | McLean | | 2005/0192675 A1 | 9/2005 | Robinson |
| 2004/0162619 A1 | 8/2004 | Blaylock et al. | | 2005/0202371 A1 | 9/2005 | McGuire |
| 2004/0162620 A1 | 8/2004 | Wyss | | 2005/0203535 A1 | 9/2005 | Parry et al. |
| 2004/0162621 A1 | 8/2004 | Crofford | | 2005/0203629 A1 | 9/2005 | Cipolletti et al. |
| 2004/0172137 A1 | 9/2004 | Blaylock et al. | | 2005/0209604 A1 | 9/2005 | Penenberg et al. |
| 2004/0172139 A1 | 9/2004 | Dwyer et al. | | 2005/0211562 A1 | 9/2005 | Rowe et al. |
| 2004/0186580 A1 | 9/2004 | Steinmann | | 2005/0216091 A1 | 9/2005 | Wasielewski |
| 2004/0186586 A1 | 9/2004 | Seyer et al. | | 2005/0228394 A1 | 10/2005 | Bihary et al. |
| 2004/0193282 A1 | 9/2004 | Hanes | | 2005/0228395 A1 | 10/2005 | Auxepaules et al. |
| 2004/0199257 A1 | 10/2004 | Dooney | | 2005/0228502 A1 | 10/2005 | Deloge et al. |
| 2004/0199259 A1 | 10/2004 | Pichon et al. | | 2005/0228503 A1 | 10/2005 | Gundolf |
| 2004/0204760 A1 | 10/2004 | Fitz et al. | | 2005/0240275 A1 | 10/2005 | Chappuis |
| 2004/0204767 A1 | 10/2004 | Park et al. | | 2005/0240276 A1 | 10/2005 | Shea et al. |
| 2004/0210316 A1 | 10/2004 | King et al. | | 2005/0246026 A1 | 11/2005 | Lewis et al. |
| 2004/0225368 A1 | 11/2004 | Plumet et al. | | 2005/0246027 A1 | 11/2005 | Metzger et al. |
| 2004/0225370 A1 | 11/2004 | Cruchet et al. | | 2005/0246028 A1 | 11/2005 | Pappas et al. |
| 2004/0225371 A1 | 11/2004 | Roger | | 2005/0246030 A1 | 11/2005 | Yao |
| 2004/0226343 A1 | 11/2004 | Babler et al. | | 2005/0256576 A1 | 11/2005 | Moskowitz et al. |
| 2004/0236428 A1 | 11/2004 | Burkinshaw et al. | | 2005/0256584 A1 | 11/2005 | Farrar |
| 2004/0243249 A1 | 12/2004 | Ishihara et al. | | 2005/0261776 A1 | 11/2005 | Taylor |
| 2004/0260396 A1 | 12/2004 | Ferree et al. | | 2005/0267584 A1 | 12/2005 | Burdulis et al. |
| 2004/0267374 A1 | 12/2004 | Friedrichs | | 2005/0267585 A1 | 12/2005 | Sidebotham |
| 2004/0267375 A1 | 12/2004 | Friedrichs | | 2005/0267590 A1 | 12/2005 | Lee |
| 2005/0004677 A1 | 1/2005 | Johnson | | 2005/0278034 A1 | 12/2005 | Johnson et al. |
| 2005/0004678 A1 | 1/2005 | Richards | | 2005/0283252 A1 | 12/2005 | Coon et al. |
| 2005/0010288 A1 | 1/2005 | Merrill et al. | | 2005/0283253 A1 | 12/2005 | Coon et al. |

| | | |
|---|---|---|
| 2005/0283254 A1 | 12/2005 | Hayes et al. |
| 2005/0288791 A1 | 12/2005 | Tornier et al. |
| 2005/0288793 A1 | 12/2005 | Dong et al. |
| 2006/0004463 A1 | 1/2006 | Lewis et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0009857 A1 | 1/2006 | Gibbs et al. |
| 2006/0015188 A1 | 1/2006 | Grimes |
| 2006/0030945 A1 | 2/2006 | Wright |
| 2006/0052876 A1 | 3/2006 | Wozencroft et al. |
| 2006/0058883 A1 | 3/2006 | Aram et al. |
| 2006/0058884 A1 | 3/2006 | Aram et al. |
| 2006/0058886 A1 | 3/2006 | Wozencroft |
| 2006/0064169 A1 | 3/2006 | Ferree |
| 2006/0074491 A1 | 4/2006 | Smith et al. |
| 2006/0085079 A1 | 4/2006 | Carroll |
| 2006/0100714 A1 | 5/2006 | Ensign |
| 2006/0129247 A1 | 6/2006 | Brwon et al. |
| 2006/0142865 A1 | 6/2006 | Hyde |
| 2006/0142867 A1 | 6/2006 | Metzger et al. |
| 2006/0149285 A1 | 7/2006 | Burgi et al. |
| 2006/0167462 A1 | 7/2006 | Raugel et al. |
| 2006/0167554 A1 | 7/2006 | Heck et al. |
| 2006/0167556 A1 | 7/2006 | Lazennec et al. |
| 2006/0167557 A1 | 7/2006 | Terrill |
| 2006/0167559 A1 | 7/2006 | Johnstone et al. |
| 2006/0167560 A1 | 7/2006 | Heck et al. |
| 2006/0173547 A1 | 8/2006 | Ensign |
| 2006/0173548 A1 | 8/2006 | Auxepaules et al. |
| 2006/0178749 A1 | 8/2006 | Pendleton et al. |
| 2006/0178750 A1 | 8/2006 | Chieng |
| 2006/0184249 A1 | 8/2006 | Tarabishy |
| 2006/0190086 A1 | 8/2006 | Clemow et al. |
| 2006/0206210 A1 | 9/2006 | Abicht et al. |
| 2006/0229734 A1 | 10/2006 | Yoon |
| 2006/0235538 A1 | 10/2006 | Rochetin et al. |
| 2006/0265079 A1 | 11/2006 | D'Alessio |
| 2007/0010890 A1 | 1/2007 | Coliazo |
| 2007/0021838 A1 | 1/2007 | Dugas et al. |
| 2007/0088443 A1 | 4/2007 | Hanssen et al. |

FOREIGN PATENT DOCUMENTS

| | | |
|---|---|---|
| EP | 0378928 | 7/1990 |
| EP | 853930 | 7/1998 |
| EP | 0947181 | 10/1999 |
| EP | 993813 | 4/2000 |
| FR | 2718953 | 10/1995 |
| FR | 2793677 | 11/2000 |
| JP | 58141847 | 8/1983 |
| WO | WO0038598 | 7/2000 |
| WO | WO 02/05732 A1 * | 1/2002 |
| WO | WO-03065939 | 8/2003 |
| WO | WO-2004080340 | 9/2004 |

* cited by examiner

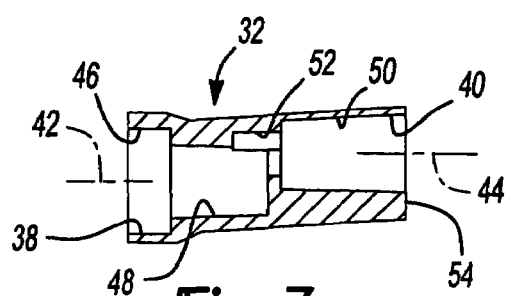
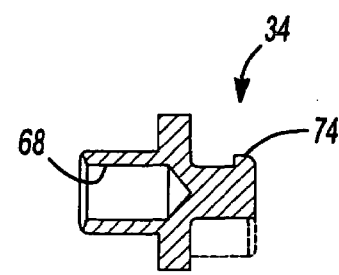
*Fig-7*  *Fig-8*
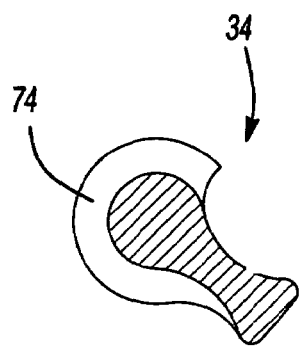
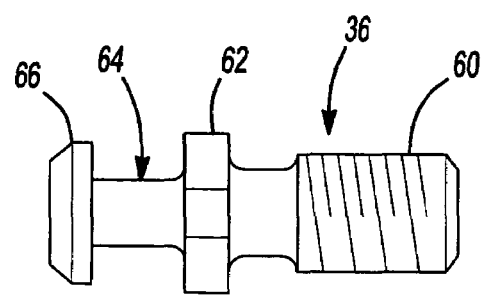
*Fig-9*  *Fig-10*
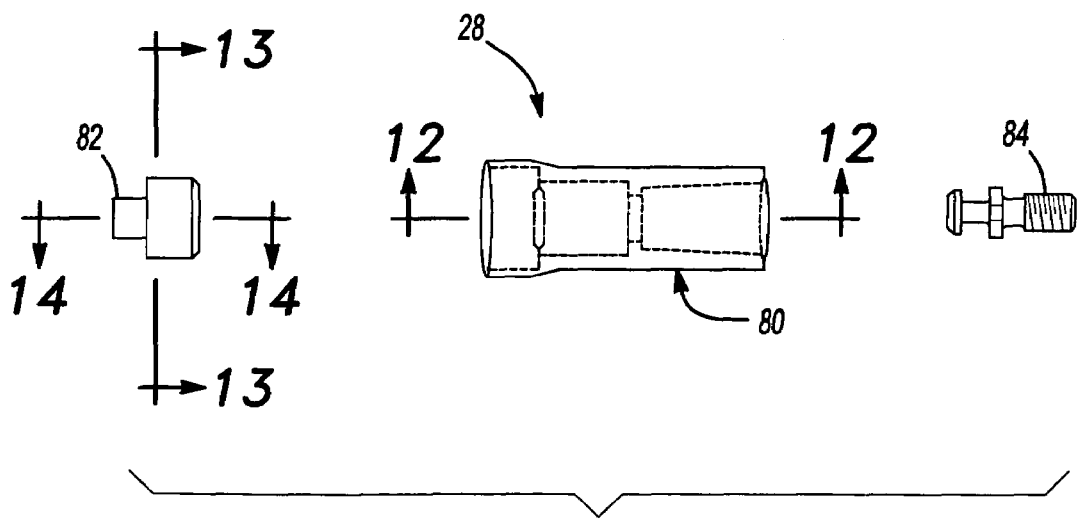
*Fig-11*

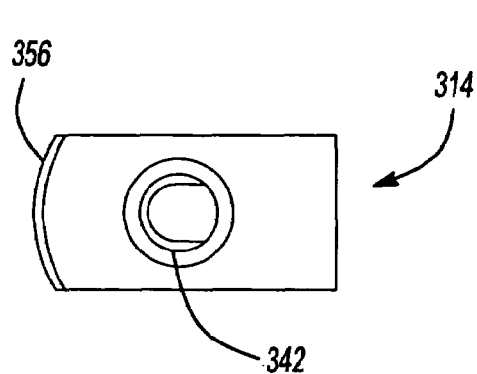
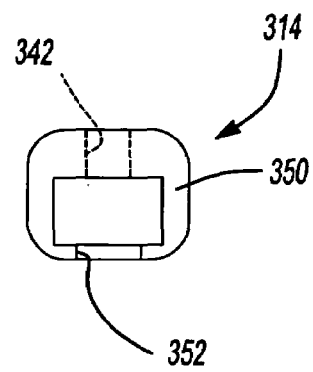
*Fig-21A*  *Fig-21B*
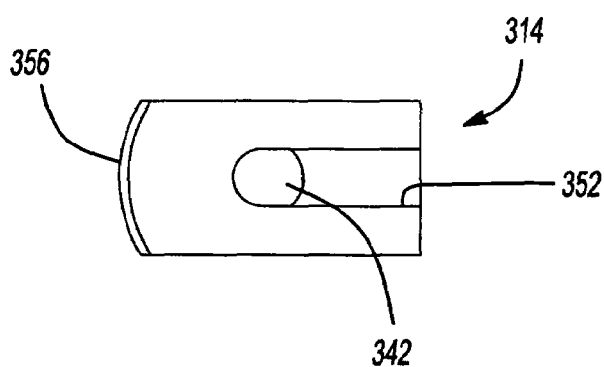
*Fig-21C*

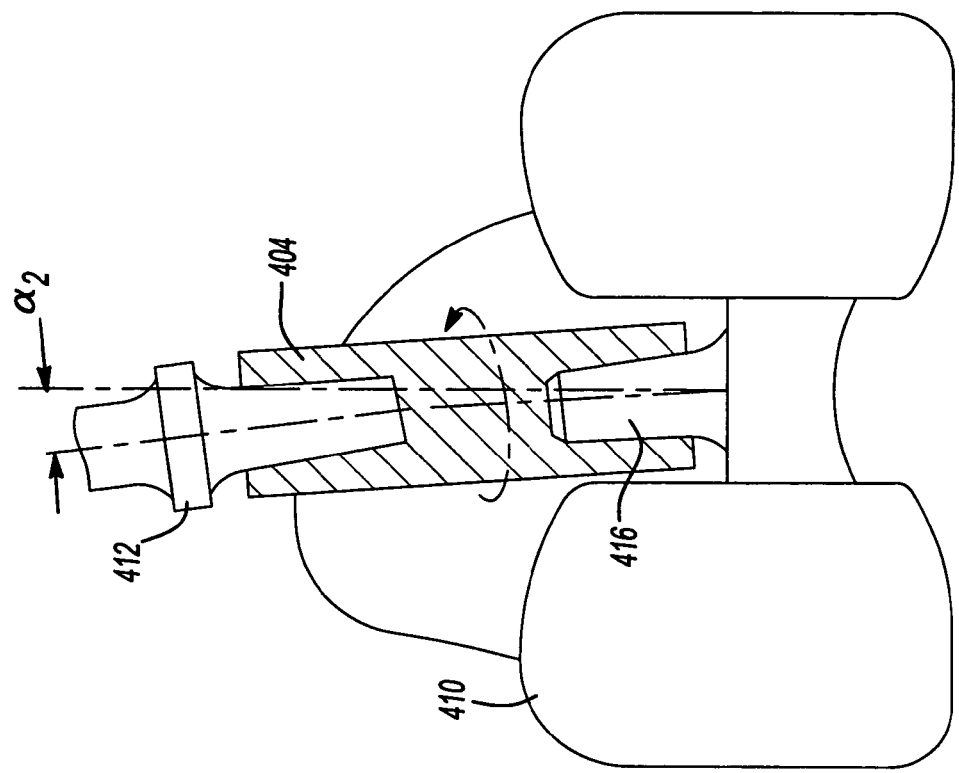
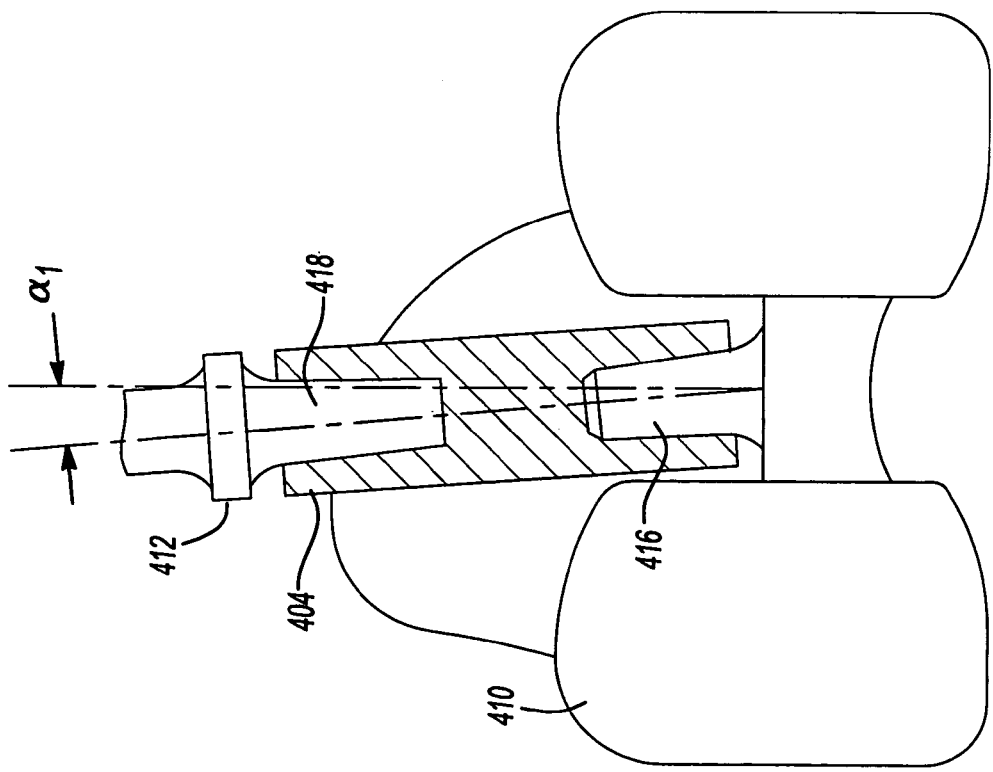

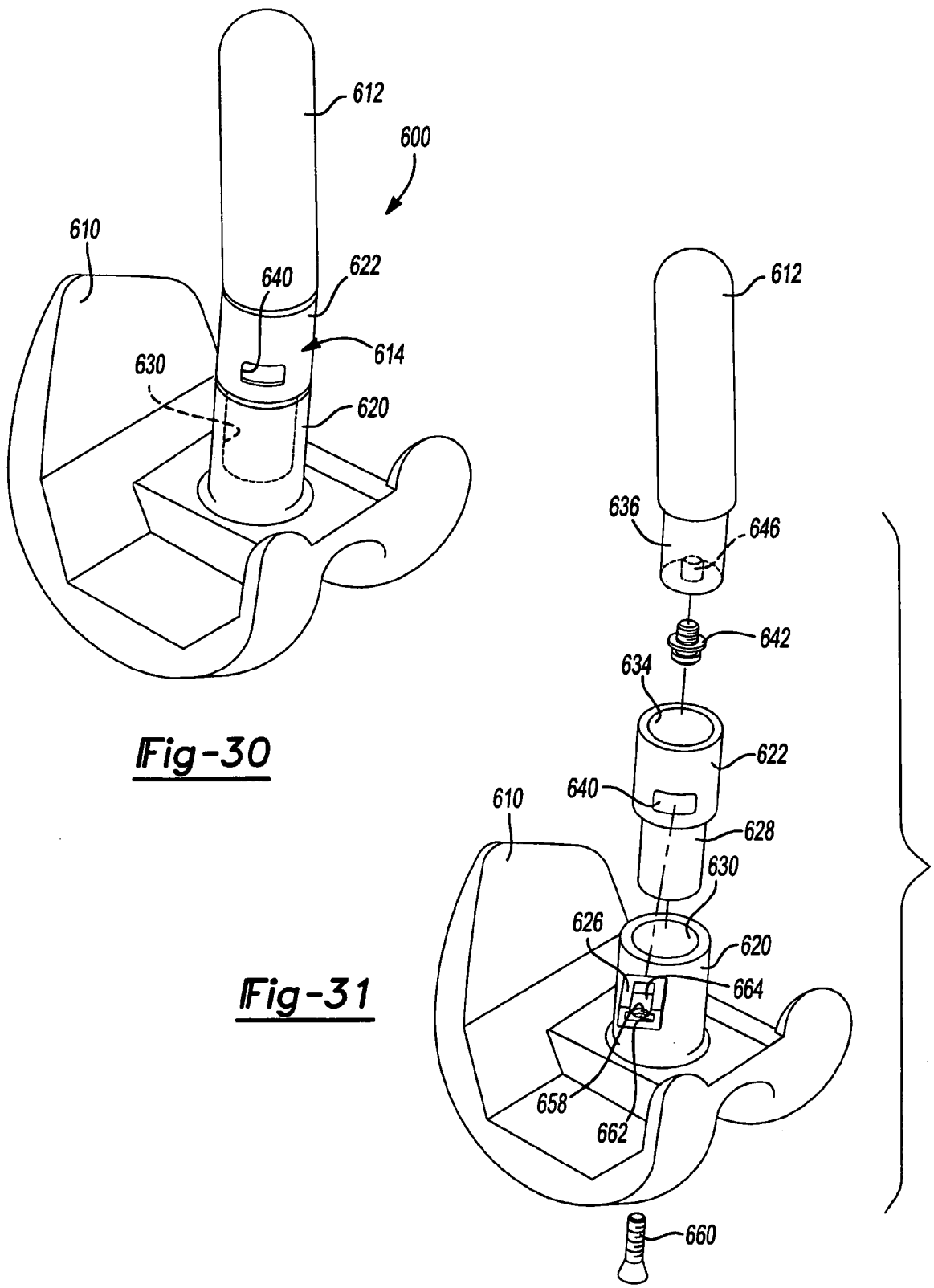

KNEE JOINT PROSTHESIS

CROSS-REFERENCE TO RELATED APPLICATIONS

This application is a continuation-in-part of U.S. Ser. No. 10/289,585, filed Nov. 7, 2002, entitled "Knee Joint Prosthesis", now U.S. Pat. No. 7,025,788, which is a continuation-in-part of U.S. Ser. No. 09/792,172, filed Feb. 23, 2001, entitled "Knee Joint Prosthesis", now abandoned, the entire contents of each which are hereby expressly incorporated herein by reference into the present application.

FIELD OF THE INVENTION

The present invention relates generally to a joint prosthesis and more particularly to a knee joint prosthesis having a femoral component and stem assembly.

BACKGROUND OF THE INVENTION

A knee joint prosthesis typically comprises a femoral component and a tibial component. The femoral component and tibial component are designed to be surgically attached to the distal end of the femur and the proximal end of the tibia respectively. The femoral component is further designed to cooperate with the tibial component in simulating the articulating motion of an anatomical knee joint. Knee joint prostheses, in combination with ligaments and muscles, attempt to duplicate natural knee motion as well as absorb and control forces generated during the range of flexion.

While known knee joint prostheses have proven to be effective in replacing the anatomical knee joint, they nevertheless have several disadvantages. For example, knee joint prostheses sometimes lack adaptability to implant conveniently with a given patient. In this regard, in a normally shaped femur, the central canal is typically offset from the center of the femoral articulating surfaces. Furthermore, the central femoral canal may present various valgus angles from one patient to another.

While knee joint prosthesis having offset femoral stems or femoral stems providing a range of valgus angles are known, they nevertheless can be subject to certain improvement.

SUMMARY OF THE INVENTION

A modular knee prosthesis includes a femoral stem having a proximal end portion. A femoral component includes a first engagement portion defined thereon wherein the femoral stem is selectively attachable to the first engagement portion of the femoral component. A connecting member includes a first end selectively attachable to the first engagement portion of the femoral component and includes a second engagement portion defined on a second end wherein the femoral stem is selectively attachable to the second engagement portion of the connecting member.

According to other features, the first and second engagement portions define a female receiving portion respectively. The proximal end portion of the femoral stem and the first end portion of the connecting member define a male insertion portion respectively. The male insertion portions each define a Morse taper. The female receiving portion defines a complementary Morse taper for alternatively receiving the male insertion portions therein. The femoral stem is selectively and alternatively attachable to the femoral component in a first orientation presenting a first valgus angle and a second orientation presenting a second valgus angle. The proximal end portion of the femoral stem is coupled to the first engagement portion of the femoral component in the first orientation. The proximal end portion of the femoral stem is coupled to the second engagement portion of the connecting member and the first end of the connecting member is coupled to the first engagement portion of the femoral component in the second orientation.

A modular knee prosthesis includes a femoral stem having a proximal end portion. A femoral component includes an engagement portion defined thereon. An adaptor body connects the femoral stem and the femoral component and establishes a relative offset between the femoral stem and the engagement portion. The adapter body includes a first end coupled to the first engagement portion of the femoral component and a second end coupled to the proximal end portion of the femoral stem. The adapter body further includes a sidewall defining an opening. A locking arrangement couples the femoral stem to the femoral component. The locking arrangement includes a locking element passing through the opening and coupling the femoral stem to the femoral component.

According to other features, the engagement portion of the femoral component defines a female receiving portion. The first end of the adapter body defines a male insertion portion having a first axis. A second end defines a female receiving portion having a second axis. The first and second axes are parallel to one another and spaced apart.

According to yet other features, a locking element threadably receives a fastener extending through the femoral component. The locking element includes an open end and a top surface having a slot intersecting the open end. The femoral stem includes a head received in the slot and defines a diameter greater than a width of the slot. The adaptor body is selectively rotatable about the first axis of the male insertion portion for presenting the femoral stem in a plurality of offset orientations around a radius defined between the first and second axes.

Additional advantages and features of the present invention will become apparent from the following description and appended claims, taken in conjunction with the accompanying drawings.

BRIEF DESCRIPTION OF THE DRAWINGS

The present invention will become more fully understood from the detailed description and the accompanying drawings, wherein:

FIG. 7 is a cross-sectional view taken along the line 7-7 of FIG. 6;

FIG. 8 is a cross-sectional view taken along the line 8-8 of FIG. 6;

FIG. 9 is a cross-sectional view taken along the line 9-9 of FIG. 6;

FIG. 10 is an enlarged view of the stem insert according to the present teachings and shown in FIG. 6;

FIG. 11 is an exploded view similar to FIG. 6, illustrating a portion of the modular tibial component of FIG. 2;

FIGS. 21A-21C are top, side and bottom views, respectively, of the locking element of the knee joint prosthesis of FIG. 19;

FIG. 24 is a partial sectional view of the knee joint prosthesis of FIG. 22 shown with a femoral stem extending at a first orientation with respect to a femoral component;

FIG. 25 is a partial sectional view of the knee joint prosthesis of FIG. 24 shown with the femoral stem extending at a second orientation with respect to the femoral component;

FIG. 30 is a perspective view of a knee joint prosthesis according to additional features;

FIG. 31 is an exploded view of the knee joint prosthesis of FIG. 30; and

DETAILED DESCRIPTION OF THE PREFERRED EMBODIMENTS

Figure 1:
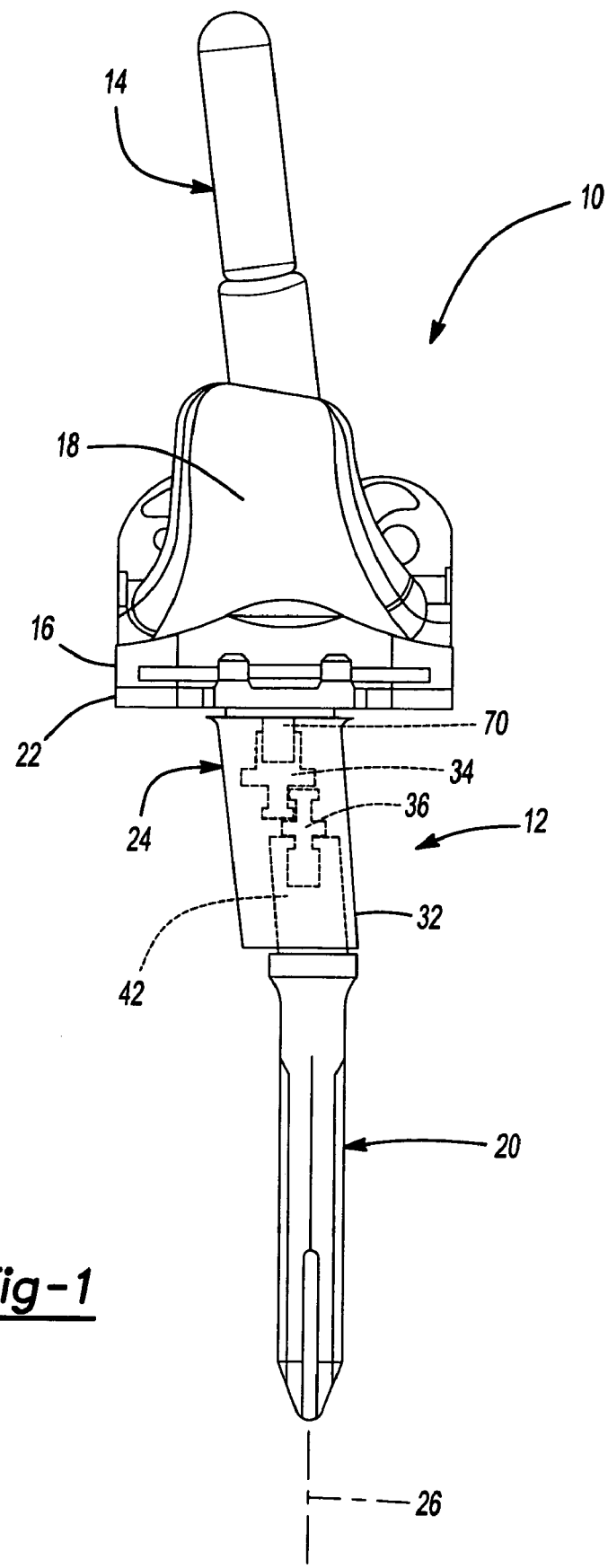
FIG. 1 is a front view illustration of a knee joint prosthesis, the knee joint prosthesis illustrated to include a first adapter assembly for providing a first predetermined offset according to the present teachings.

With initial reference to FIG. 1, a knee joint prosthesis constructed in accordance with the teachings of a preferred embodiment of the present invention is illustrated and generally identified at reference number 10. The knee joint prosthesis 10 is generally shown to include a tibial component 12 and a femoral component 14. The tibial component 12 supports a bearing 16 which engages an articulation surface 18 of the femoral component 14. Insofar as the present invention is concerned, it will be understood that the femoral component 14 and the bearing 16 shown in FIG. 1 are conventional in construction.

The tibial component 12 illustrated in FIG. 1 will be understood to be modular in construction and generally include a stem 20, a tray 22, and a first adapter assembly 24. In a manner which will be discussed more fully below, the adapter assembly 24 connects the tray 22 and the stem 20 so as to provide an offset to the stem 20 in the transverse plane. Explaining further, when the stem 20 is attached to the tray 22 through the first adapter assembly 24, a central axis of the stem 20 is offset from a central axis 27 of a downwardly extending extension 30 of the tray 22. In the embodiment illustrated, the first adapter assembly 24 provides a first offset of approximately 5 mm. It will become apparent below that the offset can be in any direction in the transverse plane.

Figure 2:
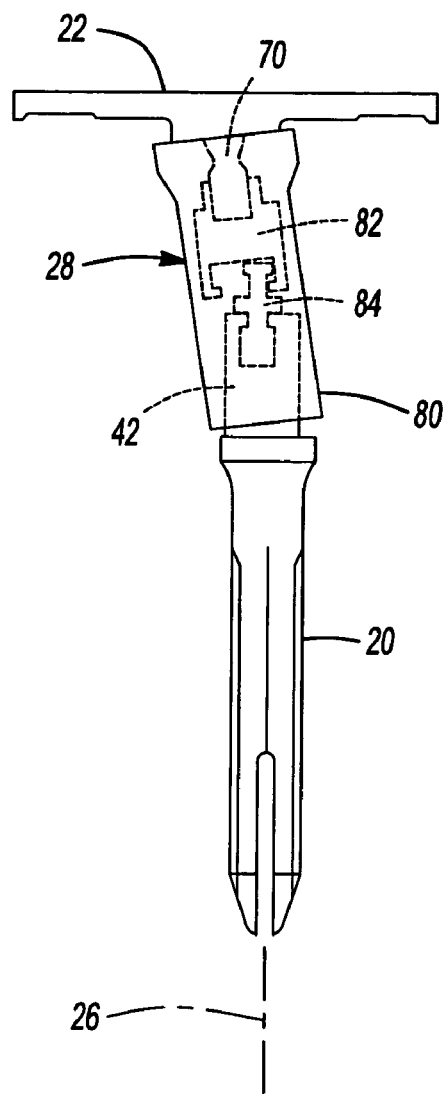
FIG. 2 is front view of a modular tibial component for a knee joint prosthesis including a second adapter assembly according to the present teachings for providing a second predetermined offset.
Figure 3:
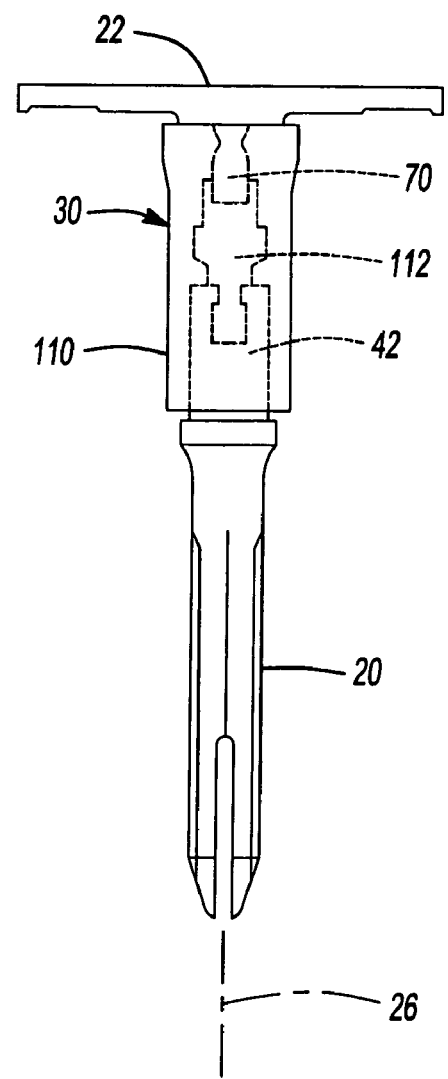
FIG. 3 is front view of a modular tibial component for a knee joint prosthesis including a third adapter assembly according to the present teachings which does not include an offset.
Figure 4:
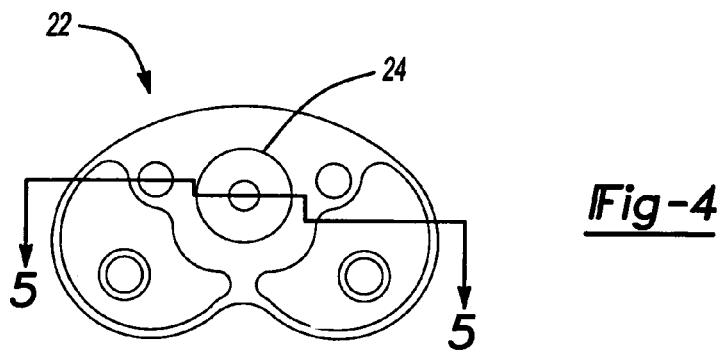
FIG. 4 is a bottom view of the tibial tray of the knee joint prosthesis of FIG. 1.
Figure 5:
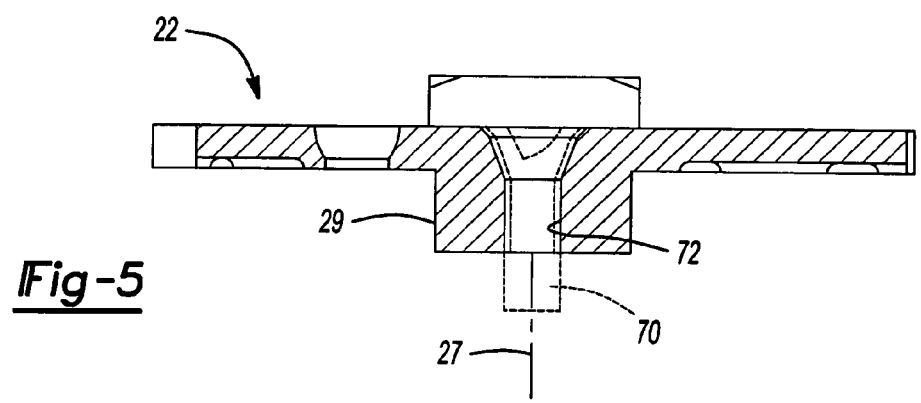
FIG. 5 is a cross-sectional view taken along the line 5-5 of FIG. 4.
Figure 6:
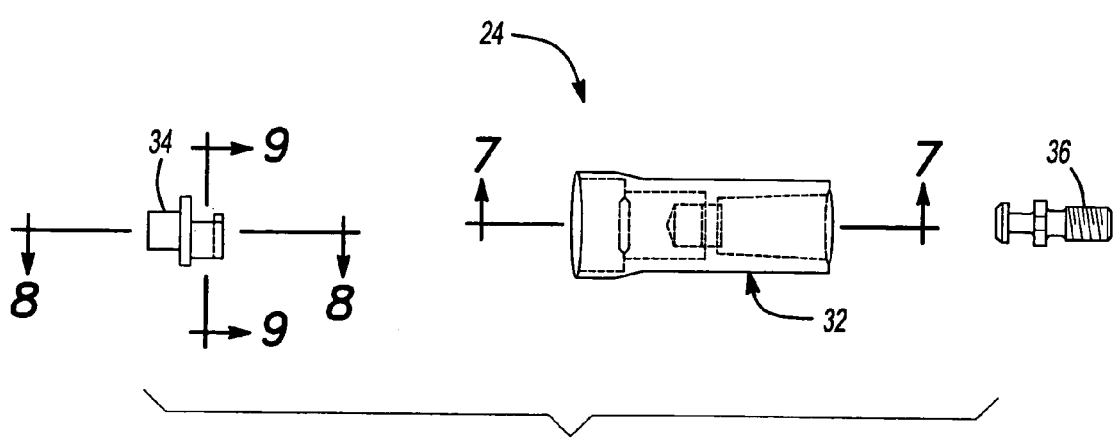
FIG. 6 is an exploded view of a portion of the modular tibial component of FIG. 1.
Figure 12:
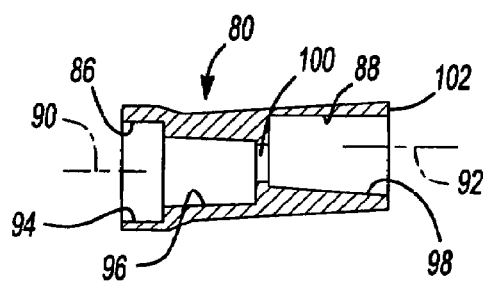
FIG. 12 is a cross-sectional view taken along the line 12-12 of FIG. 11.

With brief reference to FIGS. 2 and 3, second and third adapter assemblies 28 and 30 according to the teachings of the preferred embodiment of the present invention are illustrated, respectively. The second and third adapter assemblies 28 and 30 are shown connecting the tray 22 and stem 20 of FIG. 1. As will be discussed more fully below, the second adapter assembly 28 provides a second offset which in the embodiment illustrated is approximately 2.5 mm. The third adapter assembly is a neutral adapter assembly 30 and does not provide any offset. Explaining further, the central axis 26 of the stem 20 is aligned with the central axis 27 of the downwardly extending extension 29 of the tray 22. It will be appreciated by those skilled in the art that the particular degrees of offset provided by the various adapter assemblies 24, 28, and 30 of the present invention are strictly a matter of design choice. Alternate offsets will be understood to fall within the scope of the present invention.

With continued reference to FIG. 1 and additional reference to FIGS. 4 through 10, the first adapter assembly 24 will be further described. The first adapter assembly 24 is illustrated to generally include an adapter body 32, a locking insert member 34 and a stem insert member 36. The adapter body 32 of the first adapter assembly 24 is shown to include a first generally cylindrical cavity 38 for receiving the downwardly extending extension 29 of the tray 22 and a second generally cylindrical cavity 40 for receiving and upwardly extending extension 42 of the stem 20. The first generally cylindrical cavity 38 includes a first central axis 42 and the second generally cylindrical cavity 40 includes a second generally cylindrical axis 44. In the embodiment illustrated, the first central axis 42 and the second central axis 44 are parallel to one another and spaced apart. Insofar as the first adapter assembly 24 provides a 5 mm offset, the first and second central axes 42 and 44 are spaced apart 5 mm.

The first generally cylindrical cavity 38 includes a first portion 46 for directly receiving the downwardly extending extension 29 of the tray 22 and a second reduced diameter portion 48 which receives the locking insert 34. The first portion 46 preferably tapers slightly as it extends into the adapter body 32 from a top end of the adapter body 32. The second generally cylindrical cavity 40 similarly includes a first portion 50 and a second portion 52 of reduced diameter. The first portion 50 preferably tapers slightly as it extends into the adapter body 32 from a lower end 54 of the adapter body 32. The second portion 52 of the second generally cylindrical cavity 40 is shown to intersect the second portion 48 of the first generally cylindrical cavity 38. In a manner to be described further below, the stem insert 36 is partially disposed within the first portion 50 and extends into the second portion 52 where it engages the locking insert member 34.

With particular reference to FIG. 10, the stem insert member 36 is illustrated to include a lower portion 60 which is externally threaded for engaging an internally threaded aperture of the upwardly extending extension 42 of the stem 20. The stem insert member 36 further includes a central portion 62 having a hexagonal or other suitable cross-section which can be engaged by a tool (not shown) for rotating the stem insert member 36 into the stem 20. Further, the stem insert member 36 includes an upper end 64 including an enlarged diameter head 66 which extends into the second portion 52 of the second generally cylindrical cavity 40.

With particular reference to the cross-sectional views of FIGS. 8 and 9, the locking insert member 34 will be further described. The locking insert member 34 includes an upper portion having an internally threaded aperture 68 and having a square, hexagonal or other suitable cross section that can be engaged by a tool (not shown). The internally threaded aperture 68 threadably receives a fastener 70 which extends through a central aperture 72 provided in the tray 22. The locking insert member 34 additionally includes a radially extending segment 74 for engaging the head 66 of the stem insert member 36.

Upon selection by the surgeon of the first adapter assembly 24, the stem insert member 36 is screwed into the stem 20. Next, the adapter body 32 is placed over the upwardly extending extension 42 of the stem 20 such that the upwardly extending portion 42 is received in a press fit within the first portion 50 of the first generally cylindrical aperture 40 and the upper end 64 of the stem insert member 36 extends into the reduced diameter second portion 52 of the second generally cylindrical cavity 40. At this point, the locking insert member 34 is inserted into the first generally cylindrical cavity 38 with the radially extending segment 74 opposite the side of the reduced diameter portion 48 which intersects the reduced diameter portion 52. Upon complete insertion, the locking insert member 34 is rotated approximately between 180° and 270° such that the radially extending portion 74 engages the enlarged head 66 of the stem insert member 36.

The adapter body 32 is rotated about the axis 27 to provide the offset in the desired direction. The first portion 46 of the first generally cylindrical cavity 38 is now press fit onto the downwardly extending extension 29 of the tray 22. The stem 20 is secured to the tray 22 by the threaded fastener 70 which extends through the aperture 72 and threadably engages the internally threaded aperture 68 of the locking insert member 34. Rotation of the threaded fastener 70 in a clockwise direction causes the locking insert member 34 to be drawn towards the tray 22 and a secure connection to be established between the tray 22 and the stem 20.

With reference now to FIGS. 2 and 11 through 14, the second adapter assembly 28 of the present invention will now be described. The second adapter assembly 28 is illustrated to generally include an adapter body 80, a locking insert member 82 and a stem insert member 84. The stem insert member 84 is identical to stem insert member 36 described above.

The adapter body 80 of the second adapter assembly 28 is shown to include a first generally cylindrical cavity 86 for receiving the downwardly extending extension 29 of the tray 22 and a second generally cylindrical cavity 88 for receiving the upwardly extending extension 42 of the stem 20. The first generally cylindrical cavity 86 includes a first central axis 90 and the second generally cylindrical cavity 88 includes a second generally cylindrical axis 92. In the embodiment illustrated, the first central axis 90 and the second central axis 92 are parallel to one another and spaced apart. Insofar as the second adapter assembly 80 provides a 2.5 mm offset, the first and second central axes 90 and 92 are spaced apart 2.5 mm.

The first generally cylindrical cavity 86 includes a first portion 94 for directly receiving the downwardly extending extension 29 of the tray 22 and a second reduced diameter portion 96 which receives the locking insert 82. As with the first adapter assembly 24, the first portion 94 preferably tapers slightly as it extends into the adapter body 80 from a top end. The second generally cylindrical cavity 88 similarly includes a first portion 98 and a second portion 100 of reduced diameter. The first portion 98 preferably tapers slightly as it extends into the adapter body 80 from a lower end 102 of the adapter body 80. The second portion 100 of the second generally cylindrical cavity 88 is shown to intersect the second portion 96 of the first generally cylindrical cavity 86.

Figure 14:
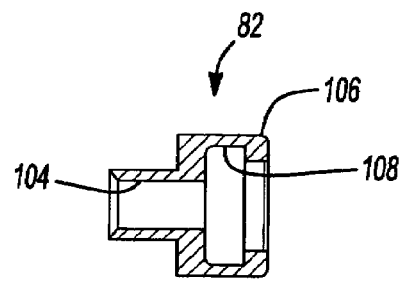
FIG. 14 is a cross-sectional view taken along the line 14-14 of FIG. 11.
Figure 13:
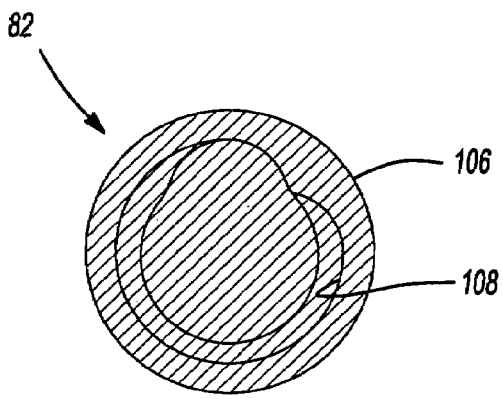
FIG. 13 is a cross-sectional view taken along the line 13-13 of FIG. 11.
Figure 16:
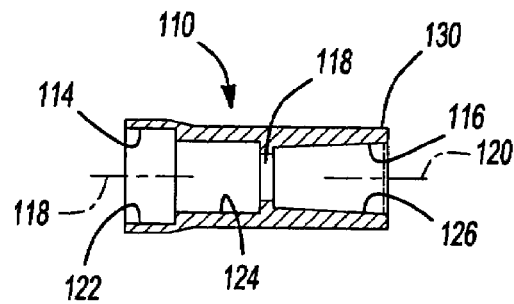
FIG. 16 is a cross-sectional view taken along the line 16-16 of FIG. 15.

With particular reference to the cross-sectional views of FIGS. 13 and 14, the locking insert member 82 will be further described. The locking insert member 82 includes an upper portion having an internally threaded aperture 104 and having a square, hexagonal or other suitable cross section that can be engaged by a tool. The internally threaded aperture 104 threadably receives the fastener 70 which extends through the central aperture 72 in the tray 22. The locking insert member 82 additionally includes a radially extending segment 106 defining a cavity 108 for engaging the head 66 of the stem insert member 36. The aperture 108 includes a non-cylindrical opening for receiving the head 66 of the stem insert member 36 and retaining the head 66 upon rotation in the manner discussed above with respect to the first adapter assembly 24.

With reference now to FIGS. 3 and 15 through 17, the third adapter assembly 30 of the present invention will now be described. The third adapter assembly 30 is illustrated to generally include an adapter body 110 and a locking insert member 112. The adapter body 110 of the third adapter assembly 30 is shown to include a first generally cylindrical cavity 114 for receiving the downwardly extending extension 29 of the tray 22 an a second generally cylindrical cavity 116 for receiving the upwardly extending extension 42 of the stem 20. The first generally cylindrical cavity includes a first central axis 118 and the second generally cylindrical cavity includes a second generally cylindrical axis 120. In the embodiment illustrated, the first central axis 118 and the second central axis 120 are coincident as the third adapter assembly 30 does not provide any offset.

The first generally cylindrical cavity 114 includes a first portion 122 for directly receiving the downwardly extending extension 29 of the tray 22 and a second reduced diameter portion 124 which receives the locking insert 112. The first portion 122 preferably tapers slightly as it extends into the adapter body 110 from an upper end. The second generally cylindrical cavity 116 similarly includes a first portion 126 and a second portion 128 of reduced diameter. The first portion 126 preferably tapers slightly as it extends into the adapter body 110 from a lower end 130 of the adapter body 110. The second portion 128 of the second generally cylindrical cavity 126 is shown to communicate with the second portion 124 of the first generally cylindrical cavity 114.

Figure 17:
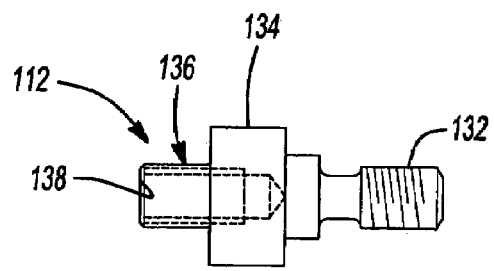
FIG. 17 is an enlarged view of the locking insert of FIG. 15.
Figure 15:
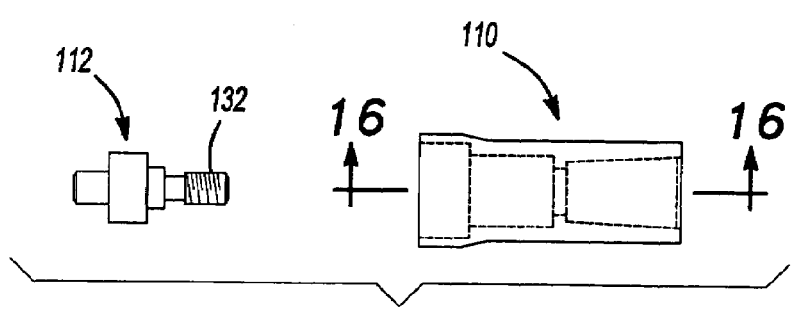
FIG. 15 is another exploded view similar to FIG. 6, illustrating a portion of the modular tibial component of FIG. 3.

With particular reference to FIG. 17, the locking insert member 112 is illustrated to include a lower portion 132 which is externally threaded for engaging the internally threaded aperture of the upwardly extending extension 42 of the stem 20. The locking insert member 112 further includes a central portion 134 and an upper portion 136. The upper portion has a square, hexagonal or other suitable cross section which can be engaged by a tool (not shown) for rotating the locking insert member 112 into the stem 20. The internally threaded aperture 138 threadably receives the fastener 70 which extends through the central aperture 72 provided in the tray 22.

Figure 18:
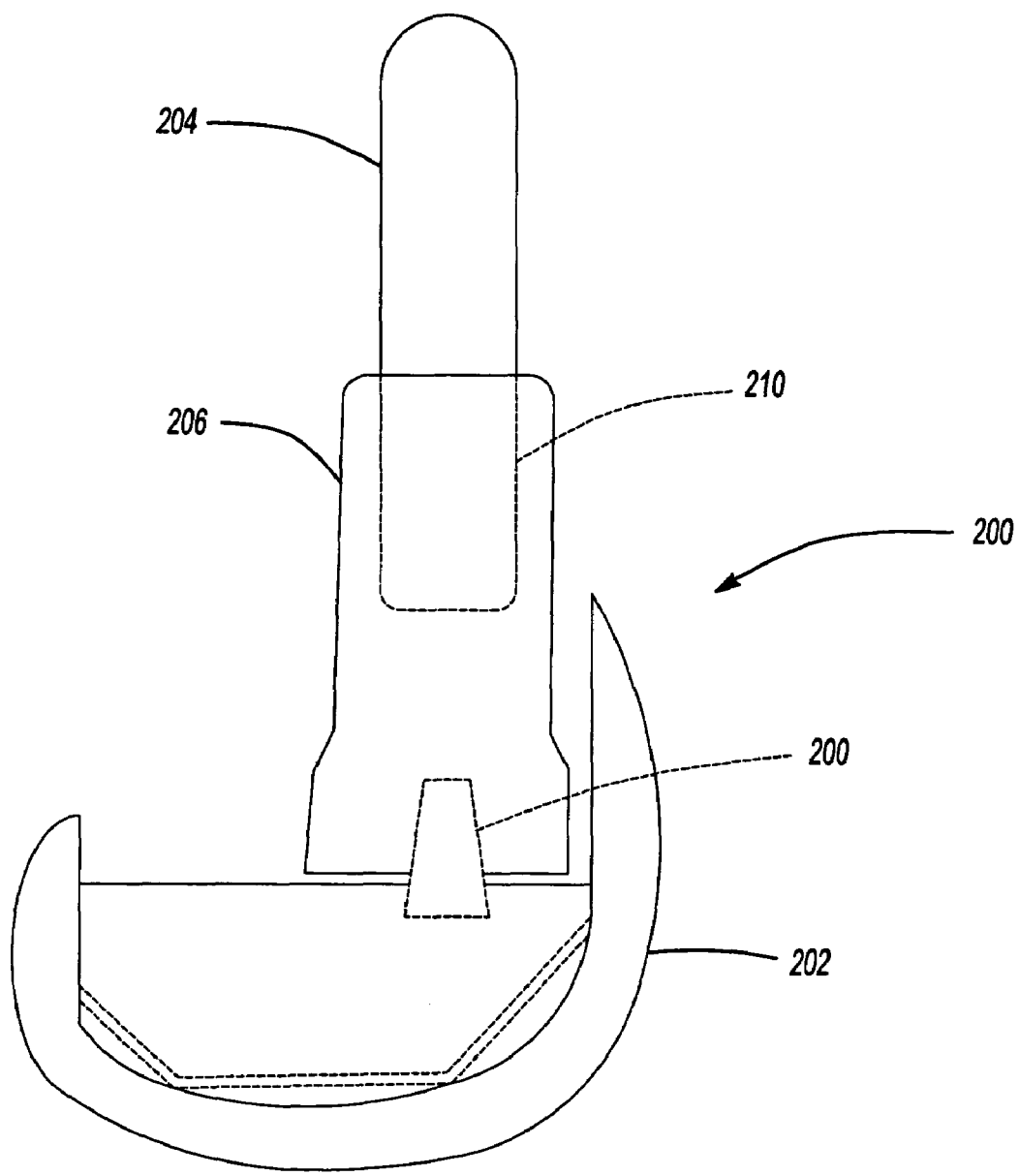
FIG. 18 is an illustration of a modular femoral component for a knee joint prosthesis according to the present teachings.

Turning to FIG. 18, a modular femoral component for a knee joint prosthesis of the present invention is generally identified at reference 200. The embodiment of FIG. 18 illustrates application of the teachings of the first preferred embodiment of the present invention adapted to a modular femoral component 200. The modular femoral component 200 includes an articulating member 202, a stem 204 and an adapter assembly 206. While not shown in great detail, it will be understood by those skilled in the art that the adapter assembly 206 is substantially identical to the first adapter assembly 24 described above. In this regard, the adapter assembly 206 connects the articulating member 202 and the stem 204 and provides an offset between an upwardly extending extension 208 of the articulating member and a downwardly extension 210 of the stem 204. The adapter assembly 206 will be understood to include an adapter body, locking insert member and stem insert member substantially identical to that described above with respect to the first adapter assembly 24. Alternatively, it will be understood that the adapter assembly of the modular femoral component 200 may be similar to either of the second and third adapter assemblies 28 and 30.

With reference to FIGS. 19, 20 and 21A through 21C, a tibial component for a knee joint prosthesis constructed in accordance with the teachings of a second preferred embodiment of the present invention is illustrated and generally identified at reference number 302. It will be understood that the knee joint prosthesis further includes a femoral component that cooperates with the tibial component 302. The particular construction of the femoral component is beyond the scope of the subject invention. One suitable femoral component is, however, shown in connection with the first preferred embodiment.

The tibial component 302 of the second preferred embodiment of the present invention will be understood to be modular in construction and generally include a stem 304, a tray 306, and an adapter assembly 308. In a manner which will be discussed more fully below, the adapter assembly 308 connects the tray 306 and the stem 304 so as to provide an offset to the stem 304 in the transverse plane. Explaining further, when the stem 304 is attached to the tray 306 through the adapter assembly 308, a central axis of the stem 304 is offset from a central axis of a downwardly extending extension 310 of the tray 306. In the embodiment illustrated, the adapter assembly 308 provides an offset of approximately 5 mm. As with the first preferred embodiment, the offset provided by the adapter assembly 308 preferably ranges from 0 mm to approximately 5 mm or more and can be in any direction in the transverse plane.

The adapter assembly 308 is illustrated to generally include an adapter body 312 and a locking member or element 314. The adapter body 312 of the adapter assembly 308 is shown to define a first cavity 316 for receiving the downwardly extending extension 310 of the tray 306 and a second cavity 318 for receiving and upwardly extending extension 320 of the stem 304. In the preferred embodiment, the first and second cavities 316 and 318 are generally cylindrical. The first cavity 316 includes a first central axis and the second cavity 318 includes a second cylindrical axis. Further, in the embodiment illustrated, the first central axis and the second central axis are parallel to one another and spaced apart. Insofar as the adapter assembly 308 provides a 5 mm offset, the first and second central axes are spaced apart 5 mm.

The first cavity 316 tapers slightly as it extends into the adapter body 312 from a top end 326 of the adapter body 312. The second cavity 318 similarly tapers slightly as it extends into the adapter body 312 from a lower end 322 of the adapter body 312. The adapter body 312 is illustrated to further define a laterally extending channel 324 which intersects both the first cavity 316 and the second cavity 318. In a manner to be described further below, the locking element 314 extends into the laterally extending channel 324 where it couples the tray 306 to the stem 304.

Figure 19:
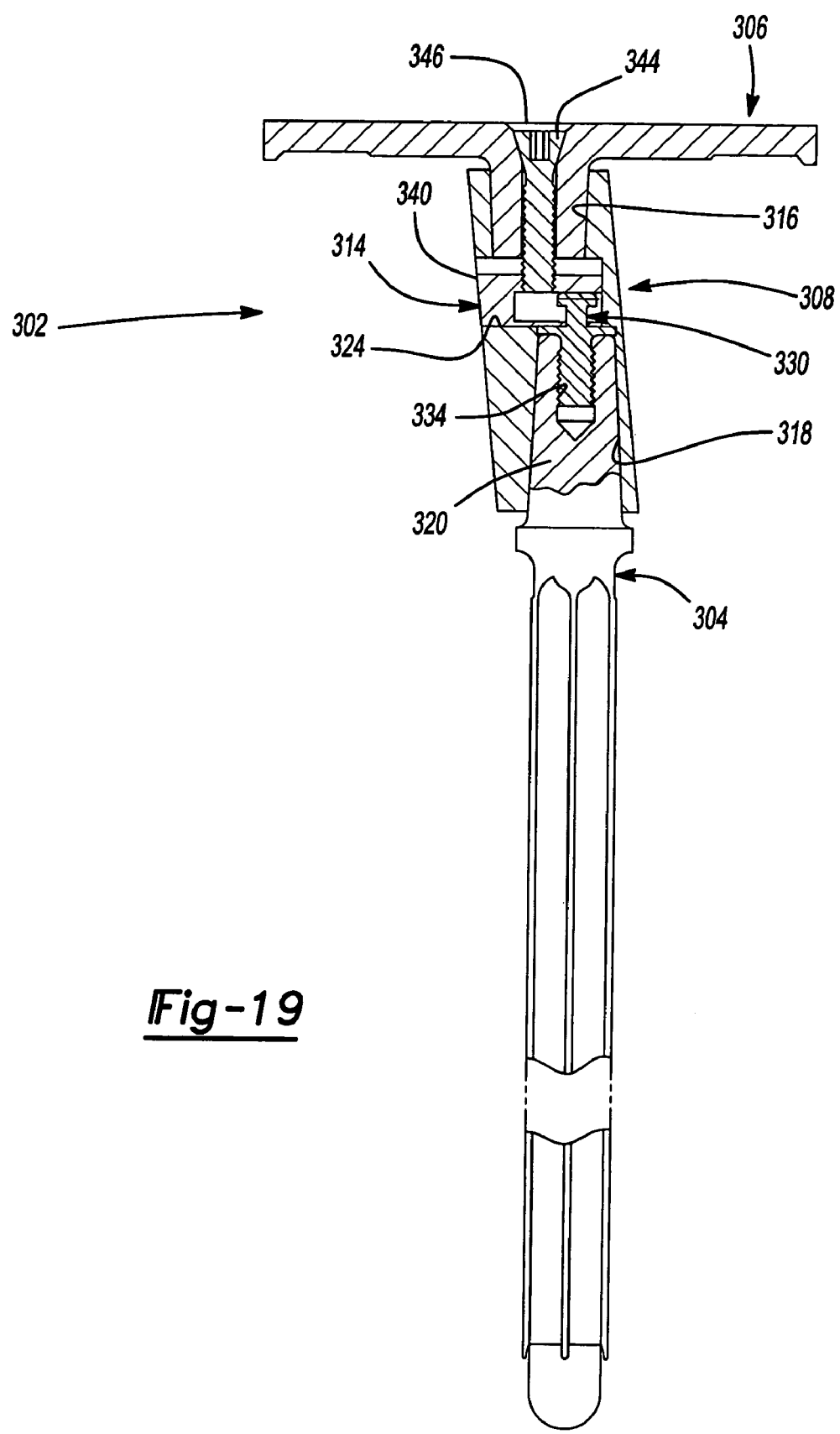
FIG. 19 is a front view illustration of a knee joint prosthesis constructed in accordance to additional features.
Figure 20:
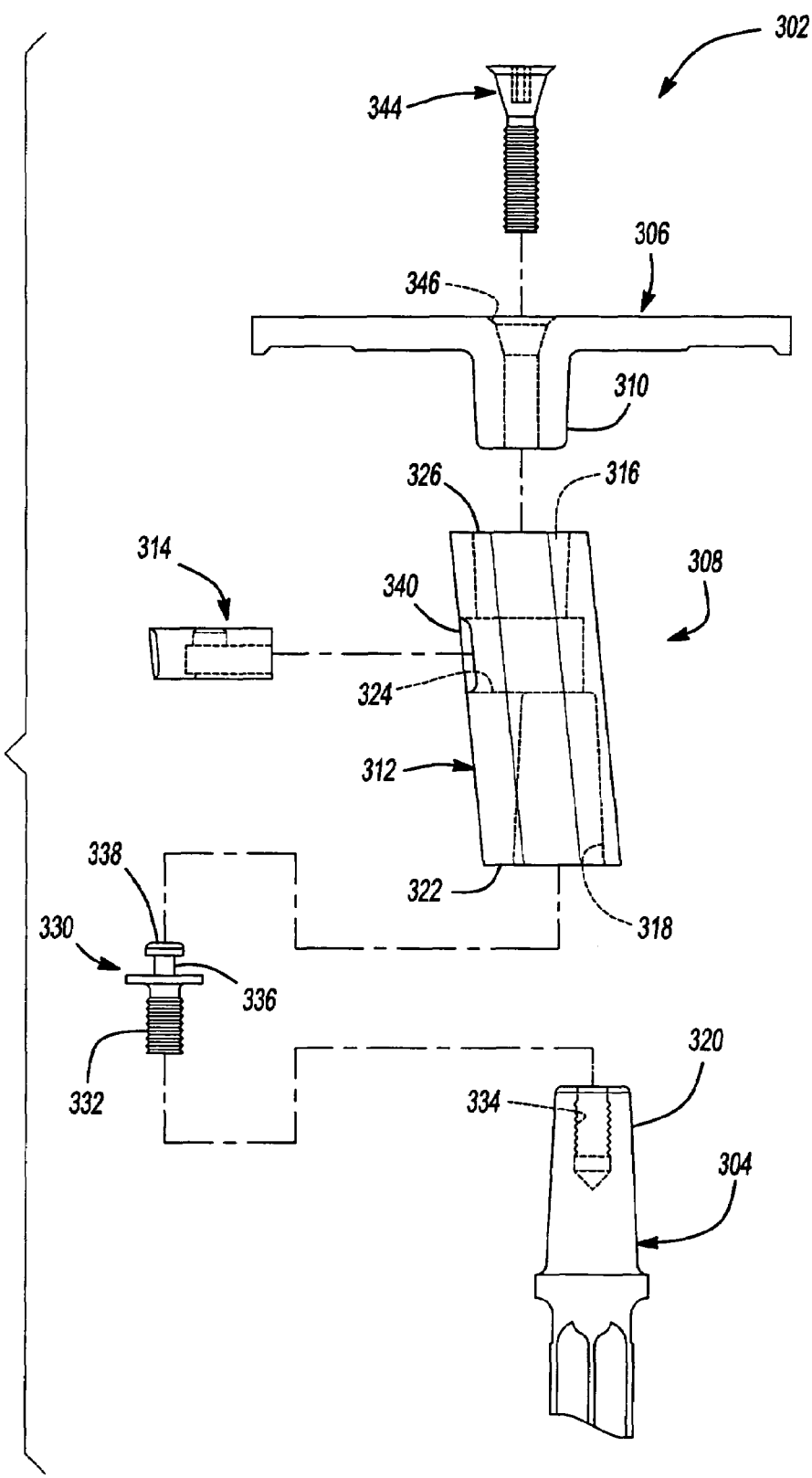
FIG. 20 is an exploded view of the knee joint prosthesis of FIG. 19.

As shown in FIGS. 19 and 20, the stem 304 is illustrated to include an upper portion that cooperatively engages with the locking element 314. In the embodiment illustrated, the upper portion of the stem 304 includes a stem insert member. Alternatively, the upper portion of the stem 304 may be integrally formed to cooperate with the locking element 314.

The stem insert member 330 is illustrated to include a lower portion 332 which is externally threaded for engaging an internally threaded aperture 334 of the upwardly extending extension 320 of the stem 304. The stem insert member 330 further includes a central portion 336 having a hexagonal or other suitable cross-section which can be engaged by a tool (not shown) for rotating the stem insert member 330 into the stem 304. Further, the stem insert member 330 includes an upper end including an enlarged diameter head 338.

The locking element 314 is sized and configured to be inserted through an opening 340 in the sidewall of the adapter body 312 and into the channel 324 for coupling of the stem 304 and the tray 306. The locking element 314 includes an upper surface (see FIG. 19) having an internally threaded aperture 342. The internally threaded aperture 342 threadably receives a fastener 344 which extends through a central aperture 346 provided in the tray 306. The fastener 344 is aligned with the central longitudinal axis of the downwardly extending portion 310 of the tray 306.

The locking element 314 is illustrated to additionally include an open end 350 and a bottom surface having a slot 352. The slot 352 intersects the open end 350. The open end 350 receives the head 338 of the stem insert 330 as the locking element 314 is inserted through the opening 340. The slot 352 accommodates the reduced diameter, central portion 336 of the stem insert 330. The head 338 of the stem insert 330 has a diameter greater than a width of the slot 352 for coupling of the stem insert 330 with the locking element 314.

The locking element 314 further includes a closed end 356. The closed end 356 is preferably convexly curved. When the locking element 314 is completely inserted into the channel 324, the closed end 356 is flush with the sidewall of the adapter body 312.

In use, the stem insert member 330 is screwed into the stem 304. Next, the adapter body 312 is placed over the upwardly extending extension 320 of the stem 304 such that the upwardly extending portion 320 is received in a press fit within the second aperture 318 and the upper end of the stem insert member 330 extends into the laterally extending channel 324.

The first cavity 316 is now press fit onto the downwardly extending extension 310 of the tray 306 with the adapter body 312 oriented to provide the offset in the desired direction. At this point, the locking element 314 is inserted into the laterally extending channel 324 through the opening 340. Upon complete insertion, the locking element 314 engages the stem insert member 330. The tray 306 is secured to the adapter body 312 by the threaded fastener 344 which extends through the aperture 346 and threadably engages the internally threaded aperture 342 of the locking element 314.

Figure 22:
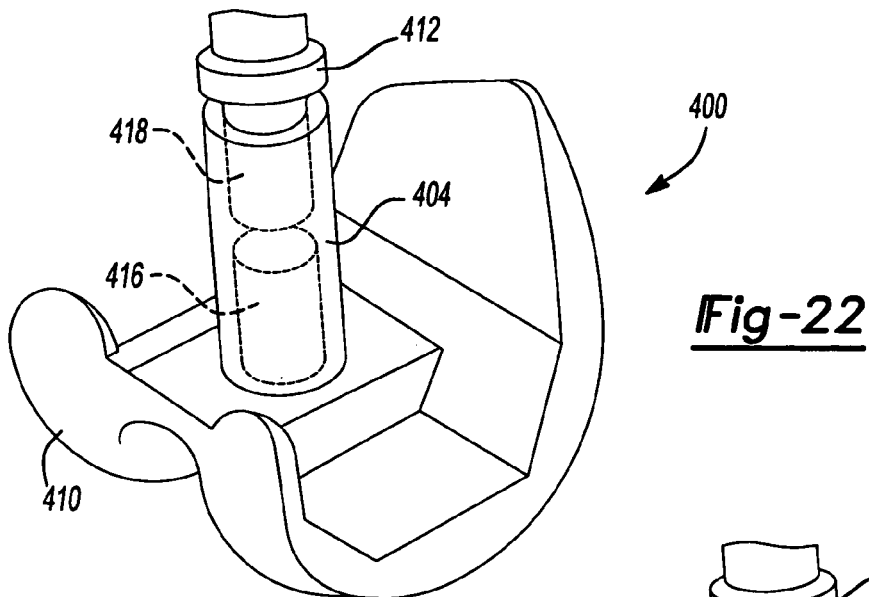
FIG. 22 is a perspective view of a knee joint prosthesis according to additional features.
Figure 23:
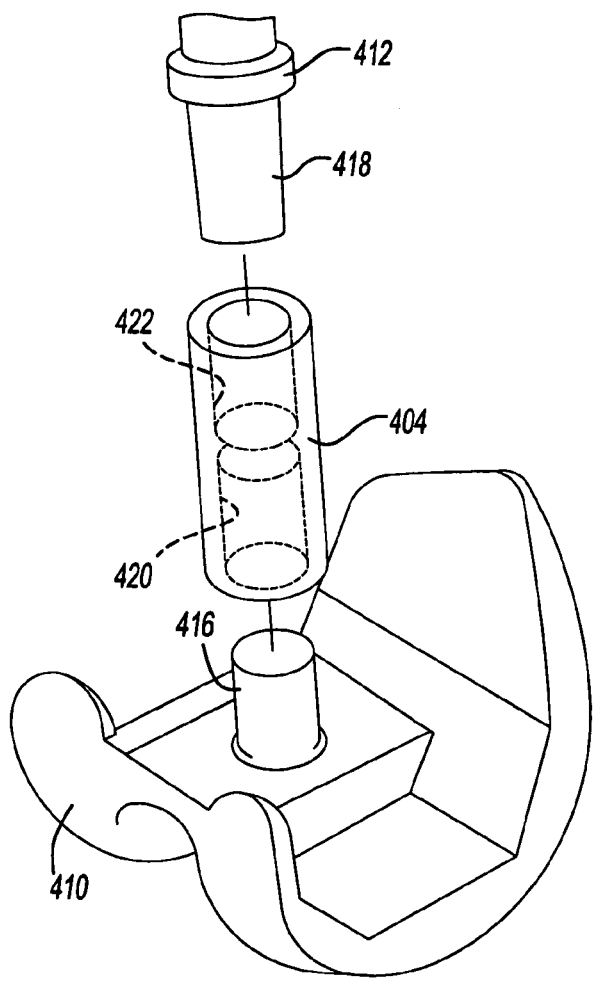
FIG. 23 is an exploded view of the knee joint prosthesis of FIG. 22.

With reference to FIGS. 22-24, a knee joint prosthesis according to other features is generally identified at reference 400. The knee joint prosthesis 400 provides a connector 404 for connecting a femoral component 410 to a femoral stem 412. As will be described, the connector 404 allows a surgeon to select a desired valgus angle between the femoral stem 412 and the femoral component 410 by rotating the connector 404 relative to the femoral component 410.

As shown, the femoral component 410 includes a male tapered extension portion 416. The male tapered extension portion 416 extends at an angle of 6° with respect to a plane of the femoral component 410 (FIGS. 24 and 25). The femoral stem 412 includes a male tapered extension portion 418. The connector 404 includes female tapered receiving portions 420 and 422 defined on opposite ends for accepting the respective male extension portions 416 and 418 therein. The mating tapered portions 416-422 may define a Morse taper for engaging the components in a secured position. The female receiving portion 420 of the connector 404 presents an offset angle with respect to a longitudinal axis of the connector 404 (FIG. 23). The offset angle is configured to be 1° although other angles may be implemented. In this way, the connector 404 may be rotated to vary the valgus angle in which the femoral stem 412 extends with respect to the femoral component 410.

As explained, the male extension portion 416 provides a 6° valgus inclination. The additional 1° provided by the connector 404 allows a surgeon to rotate the connector 404 relative to the femoral component 410 to achieve a valgus angle between 5° ($\alpha_1$, FIG. 24) and 7° ($\alpha_2$, FIG. 25). It is appreciated that the connector may be configured to accommodate other ranges of angles as necessary. Moreover, the male extension portion 416 may extend at other angles with respect to a plane of the femoral component 410. As a result, a valgus angle may be achieved for a wide range of patients.

Figure 26:
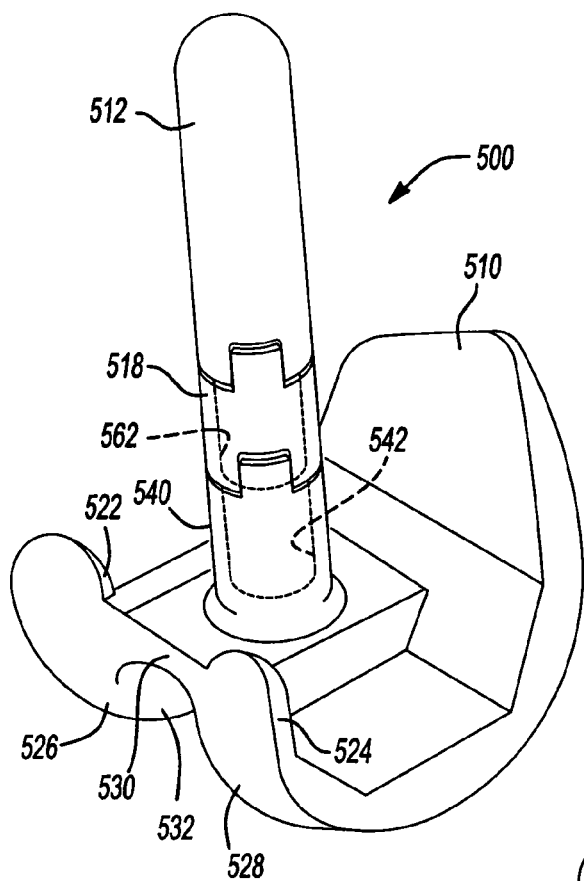
FIG. 26 is a perspective view of a knee joint prosthesis according to additional features.
Figure 27:
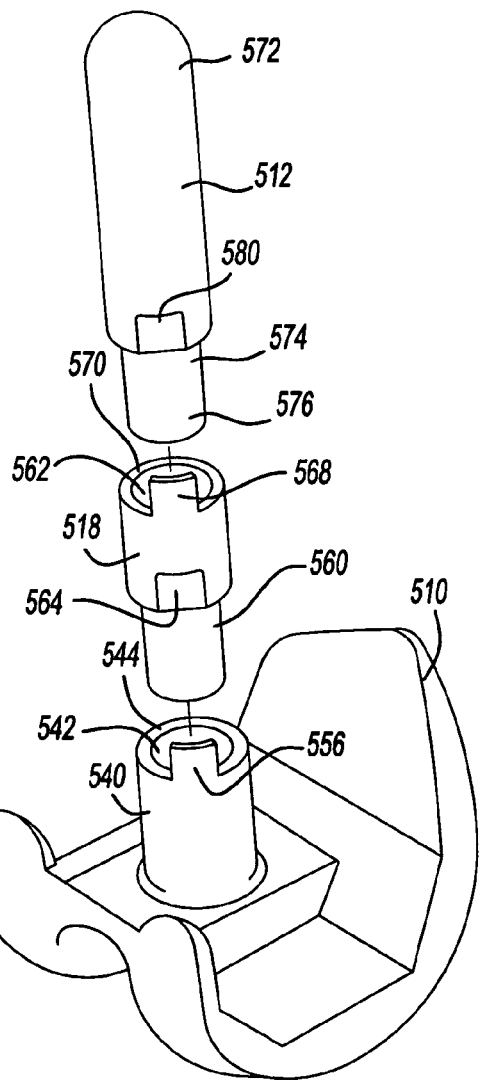
FIG. 27 is an exploded view of the knee joint prosthesis of FIG. 26.
Figure 29:
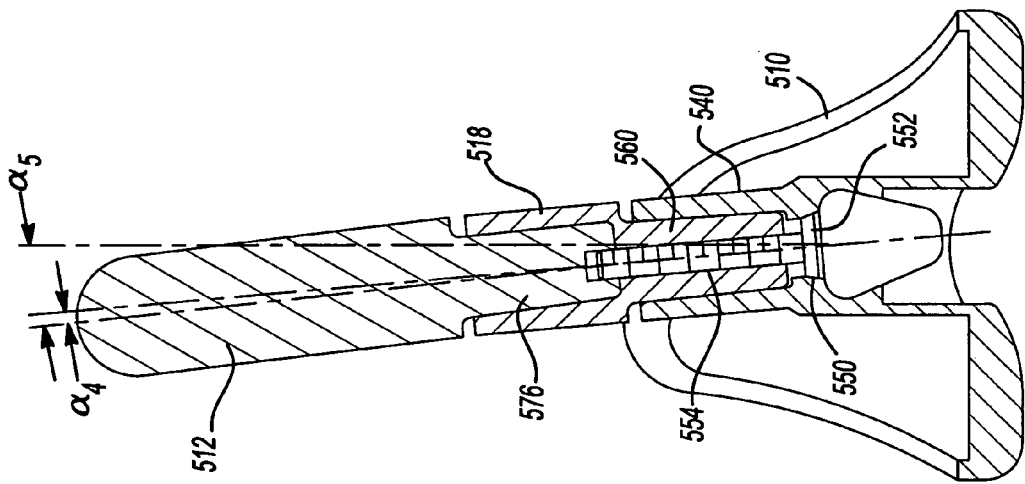
FIG. 29 is a sectional view of the knee joint prosthesis of FIG. 26 shown with a connecting member assembled between the femoral stem and the femoral component according to a second orientation.
Figure 28:
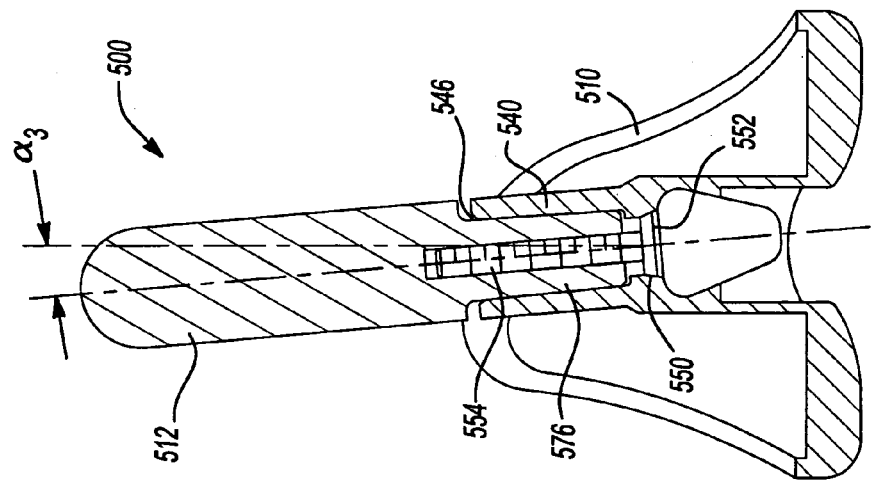
FIG. 28 is a sectional view of the knee joint prosthesis of FIG. 26 shown with a femoral stem connected directly to a femoral component according to a first orientation.

With reference now to FIGS. 26-29, a knee joint prosthesis according to other features is generally identified at reference 500. The knee joint prosthesis 500 generally includes a femoral component 510, a femoral stem 512 and a connecting member 518. As will be described, the femoral component 510 is operable to selectively receive the femoral stem 512 in a first orientation to achieve a first valgus angle (FIG. 28). In a second orientation, the femoral component 510 is operable to selectively receive the connecting member 518 having the femoral stem 512 extending from an opposite end to achieve a second valgus angle (FIG. 29).

The femoral component 500 will now be described in greater detail. The femoral component 500 includes a first condylar portion 522 and a second condylar portion 524 that provide a first femoral bearing surface 526 and a second femoral bearing surface 528, respectively. The first and second condylar portions 522 and 524 of the femoral component 510 are interconnected by an inner condylar portion 530 that defines an intercondylar recess 532.

A first engagement portion 540 extends from the femoral component 510. The first engagement portion 540 includes a generally cylindrical body and defines a female tapered receiving portion 542 (FIGS. 26 and 27). An upper rim 544 includes a chamfered surface 546 (FIG. 28) leading into the female receiving portion 542. A retaining ledge 550 (FIGS. 28 and 29) is formed on a terminal end of the female receiving portion 542. The retaining ledge 550 is adapted to support a fastener head 552 of a threaded fastener 554 in an assembled position. A locating finger 556 is defined on the upper rim 544 of the receiving portion 542 for locating a received component (femoral stem 512 or connecting member 518) in one rotational orientation as will be described.

With particular reference to FIG. 27, the connecting member 518 generally includes a cylindrical body portion having a first end defining a male tapered insertion portion 560 and a second end defining a female tapered receiving portion 562. A recess 564 is formed on a radial outer surface of the connecting member 518 for receiving the locating finger 556 of the first engagement portion 540 in an engaged position. As a result, the connecting member 518 may only be received in one orientation and is precluded from rotating about its axis in an assembled position with the femoral component 510. A locating finger 568 is formed on an upper rim 570 of the second end of the connecting member 518.

The femoral stem 512 includes a longitudinal body portion having a distal end portion 572 and a proximal end portion 574. The proximal end portion 574 defines a male tapered insertion portion 576 for being selectively received in one of the female tapered receiving portions 562 and 542 of the connecting member 518 and the femoral component 510, respectively. The proximal end 574 further includes a recess 580 for receiving one of the locating fingers 568 and 556 extending from the connecting member 518 and the femoral component 510 respectively.

With further reference now to FIG. 28, the knee joint prosthesis 500 will be described in further detail. In one arrangement, the insertion portion 576 of the femoral stem 512 may be coupled directly to the engagement portion 540 of the femoral component 510. More specifically, the male insertion portion 576 may be inserted into the female tapered receiving portion 542 for achieving a first orientation between the femoral stem 512 and the femoral component 510. During insertion, the locating finger 556 of the engagement portion 540 is aligned to be received within the recess 580 of the femoral stem 512 (FIG. 27) to achieve proper orientation. The Morse tapered fit between the respective tapered portions 542 and 576 maintains a secure fit.

The femoral component 510 is provided with a first valgus inclination. Specifically, the engagement portion 540 extends at an angle $\alpha_3$ with respect to a transverse plane of the femoral component 510. As a result, a longitudinal axis of the femoral stem 512 may be oriented at the first valgus inclination provided by the femoral component 510 in the first arrangement. The first valgus inclination may be configured to be about 5 degrees for example. It is appreciated that the femoral component 510 may be configured with a first engagement portion 540 for achieving other inclinations.

In some instances it may be necessary to provide a greater inclination between the longitudinal axis of the femoral stem 512 and the femoral component 510. In a second arrangement, as illustrated in FIG. 29, the connector 518 is utilized between the stem 512 and the femoral component 510. In the second arrangement, the male insertion portion 560 of the connector 518 is received into the female receiving portion 542 of the femoral component 510. The male insertion portion 576 of the femoral stem 512 is received into the female receiving portion 562 (FIG. 27) of the connector 518. The respective locating fingers 556 and 568 of the femoral component 510 and the connector 518 are aligned to be received in respective recesses 564 and 580 of the connector 518 and the femoral stem 512.

With continued reference FIG. 29, in the second arrangement, the femoral stem 512 is oriented in a second inclination with respect to the femoral component 510. As previously described, the first engagement portion 540 of the femoral component 510 provides a first inclination (yielding an $\alpha_3$ valgus angle, FIG. 28). The connector 518 provides an additional inclination $\alpha_4$ when coupled to the femoral component 510. In this way, the respective inclinations $\alpha_3$ and $\alpha_4$ provided by the femoral component 510 and the connector 518, respectively, achieve a combined angle $\alpha_5$. For example, the connector 518 may be configured to provide about a 2 degree inclination ($\alpha_4$) when coupled to the femoral component 510. As a result, about a 7 degree valgus angle ($\alpha_5$) may be achieved when implementing a 2 degree connector 518 with a 5 degree femoral component 510. Again, it is appreciated that the inclination of 2 degrees is merely exemplary and a series of connectors may be provided having a range of inclinations. The threaded fastener 554 is utilized for the first and second arrangements to further secure respective components 510, 512 and 518.

It is appreciated that the respective female tapered receiving portions 542 and 562 of the femoral component 510 and the connector 518 are substantially similar such that the femoral stem 512 may be selectively and alternatively coupled with either of the femoral component 510 and the connector 518. Moreover, it is understood that the male insertion portions may alternatively be configured as female receiving portions and, likewise the female receiving portions configured as male insertion portions.

Figure 32:
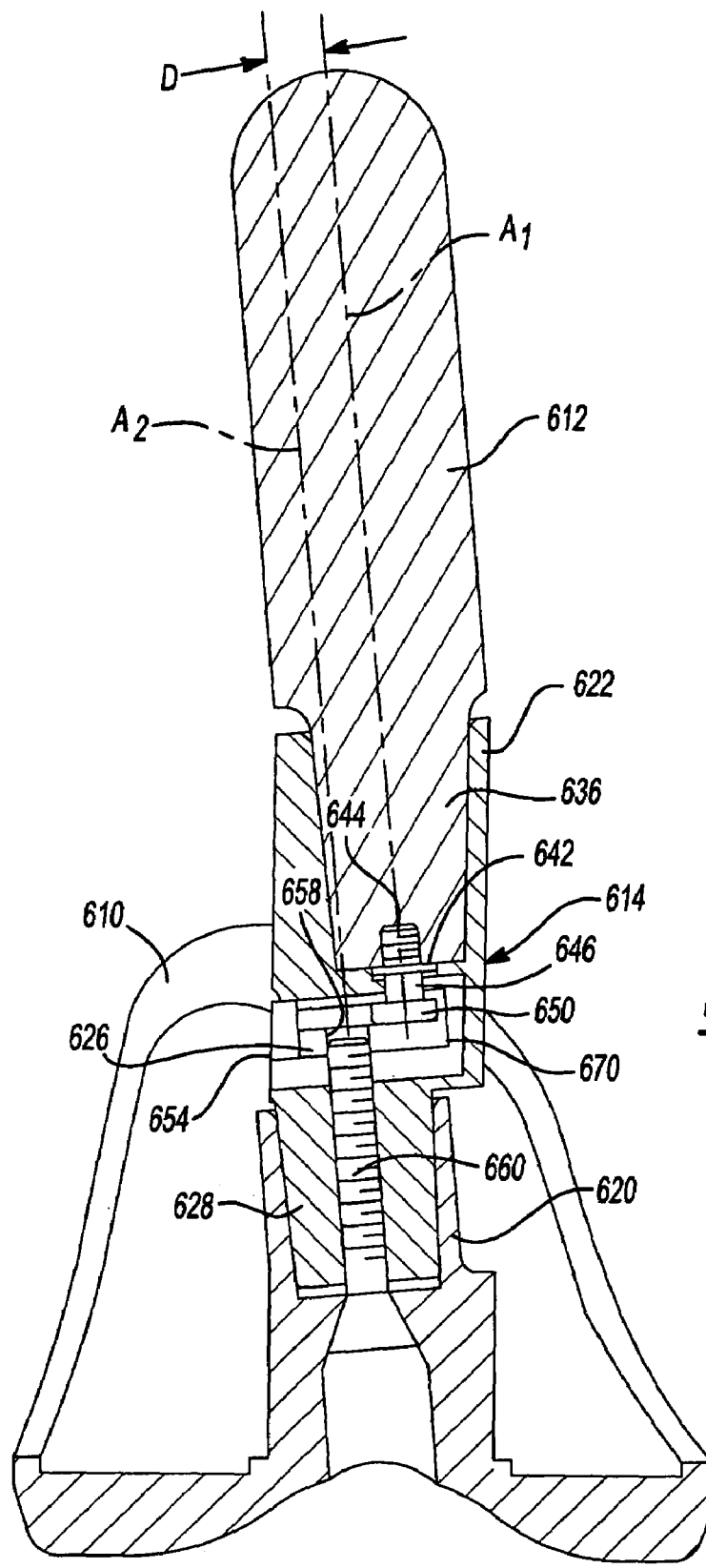
FIG. 32 is a sectional view of the knee joint prosthesis of FIG. 30.

Turning now to FIGS. 30-32, a knee joint prosthesis according to additional features is shown and generally identified at reference 600. The knee joint prosthesis 600 will be understood to be modular in construction and generally include a femoral component 610, a femoral stem 612 and an adapter assembly 614. As will be described more fully below, the adapter assembly 614 connects the femoral component 610 to the femoral stem 612 so as to provide an offset to the femoral stem 612 in the transverse plane. Explained further, when the femoral stem 612 is attached to the femoral component 610 through the adaptor assembly 614, a central axis $A_1$ of the stem 612 is offset from a central axis $A_2$ of a female receiving portion 620 extending from the femoral component 610 (FIG. 32). In the exemplary knee joint prosthesis illustrated, the adaptor assembly 614 provides an offset D of approximately 5 mm. A series of adapter assemblies may be provided to allow a plurality of offsets for a given patient. In this way, the offset D provided by a given adapter assembly preferably ranges from 0 mm to approximately 5 mm or more and can be in any direction in the transverse plane.

The adapter assembly 614 is illustrated to generally include an adaptor body 622 and a locking member or element 626. The adaptor body 622 of the adapter assembly 614 is shown to include a first end defining a male tapered insertion portion 628 adapted for insertion into a female tapered receiving portion 630 of the femoral component 610. The adaptor body 622 further includes a second end defining a female tapered receiving portion 634 adapted to receive a male tapered insertion portion 636 extending from the femoral stem 612. The female receiving portion 630 of the femoral component 610 defines the second central axis $A_2$. Similarly, the female receiving portion 634 of the adaptor body 622 defines the first central axis $A_1$. In the example illustrated in FIG. 32, the first central axis $A_1$ and the second central axis $A_2$ are parallel to one another and spaced apart. Insofar as the adapter assembly 614 provides a 5 mm offset, the first and the second central axes $A_1$ and $A_2$, respectively, are spaced apart 5 mm. It is appreciated that the first and second axes $A_1$ and $A_2$ may alternatively present an angle therebetween.

The female receiving portion 634 of the adapter body 622 tapers slightly as it extends into the adapter body 622 from a top end. The female receiving portion 630 of the femoral component 610 similarly tapers slightly as it extends into the femoral component 610 from a top end. The adapter body 622 is illustrated to further define a laterally extending channel 640 extending into the adapter body 622 from an outer surface. As will be described in detail below, the locking element 626 extends into the laterally extending channel 640 where it couples the femoral component 610 to the stem 612.

As illustrated in FIG. 32, the stem 612 includes a lower portion that cooperatively engages the locking element 626. A stem insert member 642 is illustrated to include a shank portion 644 which is externally threaded for engaging an internally threaded aperture 646 of the male insertion portion 636. The stem insert member 642 further includes a central portion 646 having a hexagonal or other suitable cross-section which can be engaged by a tool (not shown) for rotating the stem insert member 642 into the stem 612. In addition, the stem insert member 642 includes an upper end including an enlarged diameter head 650.

The locking element 642 is sized and configured to be inserted through an opening 654 in the sidewall of the adapter body 622 and into the channel 640 for coupling of the femoral component 610 and the stem 612. The locking element 626 includes a lower surface having an internally threaded aperture 658. The internally threaded aperture 658 threadably receives a fastener 660 which extends through a central aperture provided in the female receiving portion 630 of the femoral component 610. The fastener 660 is aligned with the central longitudinal axis $A_2$ of the female receiving portion 630 of the femoral component 610.

The locking element 626 is illustrated to additionally include an open end 662 and an upper surface having a slot 664. The slot 664 intersects the open end 662. The open end 662 receives the head 650 of the stem insert 642 as the locking element 626 is inserted through the opening 662. The slot 664 accommodates the reduced diameter, central portion 646 of the stem insert 642. The head 650 of the stem insert 642 has a diameter greater than a width of the slot 664 for coupling of the stem insert 642 with the locking element 626.

The locking element 626 further includes a closed end 670. The closed end 670 may be convexly curved. When the locking element 626 is completely inserted into the channel 640, the closed end 670 is flush with the sidewall of the adapter body 622.

In use, the stem insert member 642 is advanced into the stem 612. Next, the male insertion portion 636 of the stem 612 is advanced into the female receiving portion 634 of the adapter body 622 such that the head portion 650 of the stem insert member 642 extends into the laterally extending channel 640. Next, the male insertion portion 628 of the adapter body 622 is received in a press fit relationship within the female receiving portion 630 of the femoral component to provide the offset D in the desired direction.

At this point, the locking element 626 is inserted into the laterally extending channel 640 through the opening 654. Upon complete insertion, the locking element 626 engages the stem insert member 642. The adapter body 622 is secured to the femoral component 610 by advancing the fastener 660 through a central bore in the female receiving portion 620 of the femoral component 610. The fastener 660 threadably engages the internally threaded aperture 658 of the locking element 626.

The adapter body 622 may be rotated about an axis defined by the fastener 660 prior to fastening to orient the stem at the desired offset for a particular patient. As a result, the stem 612 may extend at a plurality of positions around a radius defined by the axes $A_1$ and $A_2$. In addition, a set of stems may be provided having various lengths suitable for a range of patients. Likewise, a set of adapter bodies may be provided for providing various offsets.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A modular knee prosthesis comprising:
   a femoral stem having a proximal end portion defining a first tapered male insertion portion;
   a femoral component having a first tapered female receiving portion defined thereon;
   an adapter body including a first end defining a second tapered male insertion portion and a second end defining a second tapered female receiving portion, the adapter body connecting said femoral stem and said femoral component and establishing a relative offset between said femoral stem and said first tapered female receiving portion, wherein said first tapered male insertion portion cooperatively mates with said second tapered female receiving portion, and wherein said first tapered female receiving portion cooperatively mates with said second tapered male insertion portion, said adapter body further including a sidewall defining an opening; and
   a locking arrangement for coupling said femoral stem to said adapter body, said locking arrangement including a locking element passing through said opening and coupling said femoral stem to said adapter body.

2. The modular knee prosthesis of claim 1 wherein said locking element further couples said femoral stem to said femoral component.

3. The modular knee prosthesis of claim 2 wherein said locking element threadably receives a fastener extending through said femoral component.

4. The modular knee prosthesis of claim 2 wherein said second male tapered insertion portion defines a first axis, and said second female tapered receiving portion defines second axis, said first and second axes being parallel to one another and spaced apart.

5. The modular knee prosthesis of claim 1 wherein said first male tapered insertion portion defines a first Morse taper connection with said second female tapered receiving portion and wherein said second male tapered insertion portion defines a second Morse taper connection with said first female tapered receiving portion.

6. The modular knee prosthesis of claim 1, further comprising a stem insert extending from said proximal end portion of said stem and wherein said locking element engages said stem insert.

7. The modular knee prosthesis of claim 6 wherein said stem insert is threadably received by said proximal end portion of said stem.

8. A modular knee prosthesis comprising:
   a femoral stem having a proximal end portion defining a first tapered male insertion portion;
   a femoral component having a first tapered female receiving portion defined thereon;
   an adapter body including a first end defining a second tapered male insertion portion and a second end defining a second tapered female receiving portion, said second tapered male insertion portion defining a first axis and said second tapered female receiving portion defining a second axis, said first and second axes being parallel to one another and spaced apart, wherein said first tapered male insertion portion cooperatively mates with said second tapered female receiving portion, and wherein said first tapered female receiving portion cooperatively mates with said second tapered male insertion portion, thereby establishing a relative offset between said first tapered male insertion portion and said first tapered female receiving portion, said adapter body further including a sidewall defining an opening; and
   a locking arrangement that couples said femoral stem to said femoral component, said locking arrangement including a locking element that passes through said opening and receives a first fastener extending from said femoral component and a second fastener extending from said stem thereby coupling said femoral stem to said femoral component.

9. The modular knee prosthesis of claim 8 wherein said first fastener is a threaded screw that threadably engages said locking element to tighten said femoral stem and said femoral component to said adapter body.

* * * * *